United States Patent
Yoon et al.

(10) Patent No.: US 11,522,919 B2
(45) Date of Patent: Dec. 6, 2022

(54) ESTABLISHING A SECURE COMMUNICATION LINK

(71) Applicant: Medtronic, Inc., Minneapolis, MN (US)

(72) Inventors: Hyun J Yoon, Vadnais Heights, MN (US); Bo Zhang, Blaine, MN (US); Robert Michael Ecker, Lino Lakes, MN (US); Ryan Wyszynski, Oak Grove, MN (US); Joseph C Green, Brooklyn Park, MN (US); David J. Peichel, Minneapolis, MN (US); Sudar Shields, Minneapolis, MN (US); Nicholas C. Wine, Minneapolis, MN (US); Drew J. Thwaites, Littleton, CO (US)

(73) Assignee: Medtronic, Inc., Minneapolis, MN (US)

( * ) Notice: Subject to any disclaimer, the term of this patent is extended or adjusted under 35 U.S.C. 154(b) by 492 days.

(21) Appl. No.: 16/263,752

(22) Filed: Jan. 31, 2019

(65) Prior Publication Data

US 2020/0252436 A1    Aug. 6, 2020

(51) Int. Cl.
*H04L 9/40* (2022.01)
*H04L 9/06* (2006.01)
(Continued)

(52) U.S. Cl.
CPC .......... *H04L 63/205* (2013.01); *H04L 9/0631* (2013.01); *H04L 63/0442* (2013.01);
(Continued)

(58) Field of Classification Search
CPC ..... A61B 5/0031; A61B 5/686; A61B 5/6869; A61N 1/37252; H04L 63/0442;
(Continued)

(56) References Cited

U.S. PATENT DOCUMENTS

| | | |
|---|---|---|
| 5,792,065 A | 8/1998 | Xue et al. |
| 6,993,393 B2 | 1/2006 | Von Arx et al. |

(Continued)

OTHER PUBLICATIONS

Search Query Report from IP.com (performed Apr. 6, 2021) (Year: 2021).*

(Continued)

*Primary Examiner* — Sharon S Lynch
(74) *Attorney, Agent, or Firm* — Shumaker & Sieffert, P.A.

(57) ABSTRACT

This disclosure is directed to devices, systems, and techniques for establishing a secure connection between two or more devices. In some examples, a device is configured for wireless communication. The device comprises signal reception circuitry configured to receive communications transmitted according to at least a first communication protocol, communication circuitry configured for wireless communication according to at least a second communication protocol, and processing circuitry electrically coupled to the signal reception circuitry and the communication circuitry. The processing circuitry is configured to receive, via the signal reception circuitry, a first signal according to the first communication protocol. In response to receiving the first signal, the processing circuitry is further configured to transmit, via the communication circuitry, a second signal according to the second communication protocol and establish a secure link according to the second communication protocol.

26 Claims, 5 Drawing Sheets

(51) Int. Cl.
*H04W 12/04* (2021.01)
*H04W 52/02* (2009.01)
*A61N 1/372* (2006.01)
*H04W 12/63* (2021.01)

(52) U.S. Cl.
CPC ............ *H04L 63/105* (2013.01); *H04L 63/18* (2013.01); *H04W 12/04* (2013.01); *H04W 52/0229* (2013.01); *A61N 1/37252* (2013.01); *H04W 12/63* (2021.01)

(58) Field of Classification Search
CPC ..... H04L 63/105; H04L 63/18; H04L 63/205; H04L 9/0631; H04W 12/04; H04W 12/50; H04W 12/63; H04W 52/0229
See application file for complete search history.

(56) References Cited

U.S. PATENT DOCUMENTS

| | | | |
|---|---|---|---|
| 7,013,178 B2 | 3/2006 | Reinke et al. | |
| 7,127,300 B2 | 10/2006 | Mazar et al. | |
| 7,155,290 B2 | 12/2006 | Von Arx et al. | |
| 7,668,596 B2 | 2/2010 | Von Arx et al. | |
| 7,725,172 B2 | 5/2010 | Rouw et al. | |
| 7,844,341 B2 | 11/2010 | Von Arx et al. | |
| 7,978,062 B2 | 7/2011 | LaLonde et al. | |
| 8,102,999 B2 | 1/2012 | Corndorf | |
| 8,326,424 B2 | 12/2012 | Bange et al. | |
| 8,649,757 B2* | 2/2014 | Roberts | H04W 4/80 455/404.1 |
| 8,886,296 B2 | 11/2014 | Patel | |
| 8,907,782 B2 | 12/2014 | Baker et al. | |
| 8,914,106 B2 | 12/2014 | Charlton et al. | |
| 8,942,795 B2 | 1/2015 | Gunderson et al. | |
| 8,995,949 B2* | 3/2015 | Roberts | H04L 63/18 455/404.1 |
| 9,277,534 B2* | 3/2016 | Yun | H04W 52/0238 |
| 9,597,525 B2 | 3/2017 | Cao et al. | |
| 9,635,536 B2* | 4/2017 | Narang | H04L 61/4511 |
| 9,687,658 B2* | 6/2017 | Wu | A61N 1/37223 |
| 9,833,628 B2* | 12/2017 | Yoder | G16H 40/67 |
| 9,854,425 B2* | 12/2017 | Narang | H04L 12/2803 |
| 9,855,433 B2* | 1/2018 | Shahandeh | G16H 40/67 |
| 9,889,305 B1* | 2/2018 | Hellman | A61N 1/3712 |
| 9,907,486 B2* | 3/2018 | Pflugh | A61B 5/0255 |
| 9,913,989 B2* | 3/2018 | Schilling | H04W 4/80 |
| 10,129,733 B2* | 11/2018 | Narang | G08B 25/001 |
| 10,158,968 B2* | 12/2018 | Stroud | H04W 4/80 |
| 10,307,599 B2* | 6/2019 | Schilling | A61N 1/37217 |
| 10,320,569 B1* | 6/2019 | Wentz | G06F 21/645 |
| 10,486,646 B2* | 11/2019 | Ledvina | H04W 12/06 |
| 10,499,238 B2* | 12/2019 | Narang | H04W 80/06 |
| 10,561,849 B2* | 2/2020 | Yoder | G16H 40/67 |
| 10,569,092 B2* | 2/2020 | Hellman | A61N 1/36514 |
| 10,759,389 B2* | 9/2020 | Ledvina | H04W 12/06 |
| 10,880,826 B2* | 12/2020 | Young | A61N 1/37276 |
| 11,019,195 B2* | 5/2021 | Ledvina | H04W 12/06 |
| 2004/0220631 A1 | 11/2004 | Burnes et al. | |
| 2005/0204134 A1 | 9/2005 | Von Arx et al. | |
| 2006/0116592 A1 | 6/2006 | Zhou et al. | |
| 2006/0269066 A1* | 11/2006 | Whitehead | H04L 9/3271 380/270 |
| 2008/0021524 A1 | 1/2008 | Goscha et al. | |
| 2008/0044014 A1 | 2/2008 | Corndorf | |
| 2008/0044025 A1 | 2/2008 | Corndorf | |
| 2008/0071328 A1 | 3/2008 | Haubrich et al. | |
| 2009/0287922 A1* | 11/2009 | Herwono | H04L 63/0853 713/155 |
| 2011/0172741 A1* | 7/2011 | Roberts | H04L 67/12 607/60 |
| 2011/0184491 A1 | 7/2011 | Kivi | |
| 2011/0245700 A1 | 10/2011 | Ghanem et al. | |
| 2012/0271380 A1* | 10/2012 | Roberts | H04L 9/088 607/60 |
| 2013/0108046 A1 | 5/2013 | Andersen | |
| 2013/0197613 A1* | 8/2013 | Kelly | A61N 1/3787 607/96 |
| 2014/0077929 A1* | 3/2014 | Dumas | G07C 9/00571 340/5.61 |
| 2014/0120841 A1* | 5/2014 | Roberts | H04W 4/80 455/41.2 |
| 2014/0189828 A1* | 7/2014 | Baghdasaryan | H04L 63/0861 726/6 |
| 2014/0214104 A1* | 7/2014 | Greenhut | A61N 1/3621 607/4 |
| 2014/0273824 A1* | 9/2014 | Fenner | H04L 63/0823 455/41.1 |
| 2015/0038080 A1* | 2/2015 | Stroud | H04W 48/16 455/41.1 |
| 2015/0065047 A1* | 3/2015 | Wu | H04W 4/80 455/41.2 |
| 2015/0117645 A1* | 4/2015 | Carlson | H04W 12/04 380/262 |
| 2015/0156749 A1* | 6/2015 | Yun | H04L 25/02 455/509 |
| 2015/0341785 A1* | 11/2015 | Young | H04W 12/50 607/60 |
| 2016/0114168 A1 | 4/2016 | Demmer et al. | |
| 2016/0210189 A1* | 7/2016 | Xhafa | H04L 1/08 |
| 2016/0330573 A1* | 11/2016 | Masoud | G06F 21/606 |
| 2016/0371961 A1* | 12/2016 | Narang | H04W 4/06 |
| 2016/0371967 A1* | 12/2016 | Narang | G08B 3/10 |
| 2016/0374124 A1* | 12/2016 | Gothe | H04B 7/24 |
| 2017/0026777 A1* | 1/2017 | Denboer | H04W 4/80 |
| 2017/0134889 A1* | 5/2017 | Stroud | G05B 15/02 |
| 2017/0216611 A1* | 8/2017 | Yoder | A61N 1/37217 |
| 2017/0312530 A1* | 11/2017 | Schilling | A61N 1/37223 |
| 2018/0028827 A1* | 2/2018 | Schilling | A61N 1/00 |
| 2018/0028828 A1 | 2/2018 | Cao et al. | |
| 2018/0043173 A1* | 2/2018 | Hellman | A61N 1/3712 |
| 2018/0063784 A1* | 3/2018 | Abraham | A61N 1/37252 |
| 2018/0070222 A1* | 3/2018 | Narang | G08B 25/001 |
| 2018/0085592 A1* | 3/2018 | Yoder | A61N 1/37217 |
| 2018/0109946 A1* | 4/2018 | Mosenia | H04W 12/50 |
| 2018/0117346 A1* | 5/2018 | Hellman | A61B 5/318 |
| 2018/0200525 A1* | 7/2018 | Schilling | H04W 4/80 |
| 2019/0036886 A1* | 1/2019 | Wu | H04W 12/71 |
| 2019/0053031 A1* | 2/2019 | Narang | H04L 61/4511 |
| 2019/0135229 A1* | 5/2019 | Ledvina | G01S 13/76 |
| 2019/0282819 A1* | 9/2019 | Schilling | A61N 1/37217 |
| 2020/0062217 A1* | 2/2020 | Ledvina | H04W 12/08 |
| 2020/0099526 A1* | 3/2020 | James | H04L 9/0662 |
| 2020/0106877 A1* | 4/2020 | Ledvina | H04M 1/72436 |
| 2020/0121937 A1* | 4/2020 | Yoder | A61N 1/37252 |
| 2020/0147401 A1* | 5/2020 | Hellman | A61B 5/318 |
| 2021/0006652 A1* | 1/2021 | Ledvina | H04L 9/30 |
| 2021/0258418 A1* | 8/2021 | Ledvina | H04W 4/026 |

OTHER PUBLICATIONS

John Padgette et al., Guide to Bluetooth Security, NIST Special Publication 800-121, Revision 2 (May 2017) (available at https://nvlpubs.nist.gov/nistpubs/SpecialPublications/NIST.SP.800-121r2.pdf) (Year: 2017).*
Search Query Report from IP.com (performed Oct. 8, 2021) (Year: 2021).*
Search Query Report from IP.com (performed Mar. 11, 2022) (Year: 2022).*
Search Query Report from IP.com (performed Jul. 15, 2022). (Year: 2022).*
Shi et al, "A 10 mm3 Inductive Coupling Radio for Syringe-Implantable Smart Sensor Nodes", IEEE Journal of Solid-State Circuits, vol. 51, No. 11, Nov. 2016, 14 pages.
(PCT/US2020/015842) PCT Notification of Transmittal of the International Search Report and the Written Opinion of the International Searching Authority, dated Apr. 28, 2020,16 pages.

* cited by examiner

ESTABLISHING A SECURE COMMUNICATION LINK

TECHNICAL FIELD

The disclosure relates to device communication and, more particularly, establishing secure communication links between two or more devices.

BACKGROUND

A computing device may be configured to transmit communications to, and receive communications from, other computing devices. These communications may include data or any information that is transmitted between devices either wirelessly or via a wired connection. Communications that are public or otherwise do not include sensitive information may be unsecured. Communications that are intended to be private to two or more devices may be encrypted such that the information contained therein is not readily available to unauthorized devices. For example, an implantable medical device (IMD) may exchange sensitive information with one or more external devices via an encrypted wireless communication link. However, communication environments outside of the medical device space may also be used to exchange sensitive information.

IMDs may be surgically implanted in a patient to monitor one or more physiological parameters of the patient and/or deliver therapy to suppress one or more symptoms of the patient. For example, an IMD may include a cardiac monitor, be configured to deliver cardiac pacing or another electrical therapy to the patient, and/or be configured to terminate tachyarrhythmia by delivery of high energy shocks. A clinician or patient may use an external device to retrieve information collected by the IMD and/or to configure or adjust one or more parameters of the monitoring and/or therapy provided by the IMD. Typically, the external device connects to the IMD via a wireless connection. In some examples, a wireless connection is established between the external device and the IMD using a Bluetooth® wireless protocol. In such an example, the external device is treated as a central device, and one or more IMDs are treated as peripheral devices.

In some examples, communications between an external device (e.g., a medical device programmer or data acquisition device) and an IMD (e.g., a pacemaker, a defibrillator, a neurostimulator, a cardiac monitor, or a drug pump, as examples) may be encrypted to secure sensitive information such as collected patient data or programming instructions that at least partially define the operation of an IMD. Secure communication involving medical devices may involve an encryption scheme known to both the external device and the IMD. For example, both the external device and the IMD may utilize a stored encryption key to encrypt and/or decrypt some or all information transmitted between the devices.

SUMMARY

In general, the disclosure is directed to devices, systems, and techniques for establishing a secure connection between two or more devices. For example, this disclosure describes techniques for using an external device to establish a secure connection between an IMD, the external device, and, in some cases, an additional external device. Prior to secure communication according to a second communication protocol, the external device may initiate a pairing procedure by emitting a signal according to a first communication protocol. While the first communication protocol is, in some examples, unknown to the IMD, the IMD is configured to sense the first signal based on electric field variations caused by the signal. During the pairing procedure, the devices may each generate at least one encryption key (e.g., session key) based on random numbers generated by the devices. The IMD may send a challenge to the external device, and based on a verification of the challenge, the devices may establish a secure link. Following the pairing procedure, the devices may securely communicate using the session keys until the secure link is terminated. For instance, the external device, or the additional external device, may be a programming device configured to communicate with the IMD to modify one or more settings of the IMD and receive patient data from the IMD.

In some examples, the communication range of the second protocol is greater than that of the first protocol. During the pairing procedure, however, communication with the IMD may be according to a reduced power mode and, consequently, reduced range implementation of the second protocol, in some cases. In some examples, subsequent to pairing, the power and communication range will no longer be reduced for secured communication with the IMD according to the second protocol. In some examples, the signal according to the first protocol is a wake-up signal for the IMD, e.g., transitions at least some circuitry, such as communication circuitry, of the IMD from a relatively lower energy consumption mode into a relatively higher energy consumption mode in which communication with one or more external devices occurs. In one example, the IMD transitions its communication circuitry from being in an off state in which the communication circuitry is not transmitting or receiving to being in an on state during which the communication circuitry is capable of transmitting and receiving. In another example, the IMD transitions from a first relatively lower energy consumption mode in which advertisement signals are transmitted at a first rate to a second relatively higher energy consumption mode in which advertisement signals are transmitted at a second, faster rate which results in increased power consumption.

The techniques of this disclosure may provide one or more advantages. For example, before the establishment of a secure link between a first device and a second device, the second device may not have access to an encryption key for encoding or decoding data exchanged with the first device. An example second device of this disclosure may initiate the generation of an encryption key which enables the second device to communicate securely with first device. The second device may send a relatively close-range signal to the first device, starting a process which generates the encryption key. By using the close-range signal, the second device decreases a probability that the signal may be fraudulently replicated by a third-party device. After the generation of the encryption key, the first device and the second device may exchange information at a relatively longer range than the close-range signal initially sent from the second device to the first device. Additionally, in some examples, the first device is configured to communicate exclusively using a particular protocol, such as a Bluetooth® protocol. At least some techniques of this disclosure allow the first device to receive and identify signals that are not transmitted using the Bluetooth® protocol, enabling the second device to initiate the pairing process using a custom, non-Bluetooth® signal that is not easily replicated by any device with Bluetooth® capabilities.

In some examples, a first device is configured for wireless communication. The first device includes signal reception circuitry configured to receive communications transmitted according to at least a first communication protocol, communication circuitry configured for wireless communication according to at least a second communication protocol, and processing circuitry electrically coupled to the signal reception circuitry and the communication circuitry. The processing circuitry is configured to receive, via the signal reception circuitry, a first signal according to the first communication protocol. In response to receiving the first signal, the processing circuitry is further configured to transmit, via the communication circuitry, a second signal according to the second communication protocol and establish a secure link according to the second communication protocol, where to establish the secure link, the processing circuitry is configured to transmit at least one signal at a first power magnitude, and where communications transmitted over the secure link are at a second power magnitude greater than the first power magnitude.

In other examples, a method includes receiving, by signal reception circuitry of a first device configured to receive communications transmitted according to at least a first communication protocol, a first signal according to the first communication protocol. In response to receiving the first signal, the method further includes transmitting, via communication circuitry, a second signal according to a second communication protocol and establishing a secure link according to the second communication protocol, where establishing the secure link comprises transmitting at least one signal at a first power magnitude, and where communications transmitted over the secure link are at a second power magnitude greater than the first power magnitude.

In other examples, a system includes a first device including signal reception circuitry configured to receive communications transmitted according to at least a first communication protocol, communication circuitry configured for wireless communication according to at least a second communication protocol, and first processing circuitry electrically coupled to the signal reception circuitry and the communication circuitry. The first processing circuitry is configured to receive, via the signal reception circuitry, a first signal according to the first communication protocol. In response to receiving the first signal, the first processing circuitry is further configured to transmit, via the communication circuitry, a second signal according to the second communication protocol. The system further includes a second device including second communication circuitry configured for wireless communication according to the first communication protocol having a first range and the second communication protocol having a second range, the second communication protocol different than the first communication protocol and the second range greater than the first range, and second processing circuitry electrically coupled to the second communication circuitry. The second processing circuitry is configured to transmit, via the second communication circuitry, the first signal to the first device according to the first communication protocol. In response to transmitting the first signal, the second processing circuitry is further configured to receive, via the second communication circuitry and from the first device, the second signal according to the second communication protocol. In response to receiving the second signal, the second processing circuitry is further configured to establish a secure link according to the second communication protocol, wherein the secure link includes the first device and at least one of the second device and a third device, where to establish the secure link, the second processing circuitry is configured to receive at least one signal at a first power magnitude, and where communications transmitted over the secure link are at a second power magnitude greater than the first power magnitude.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
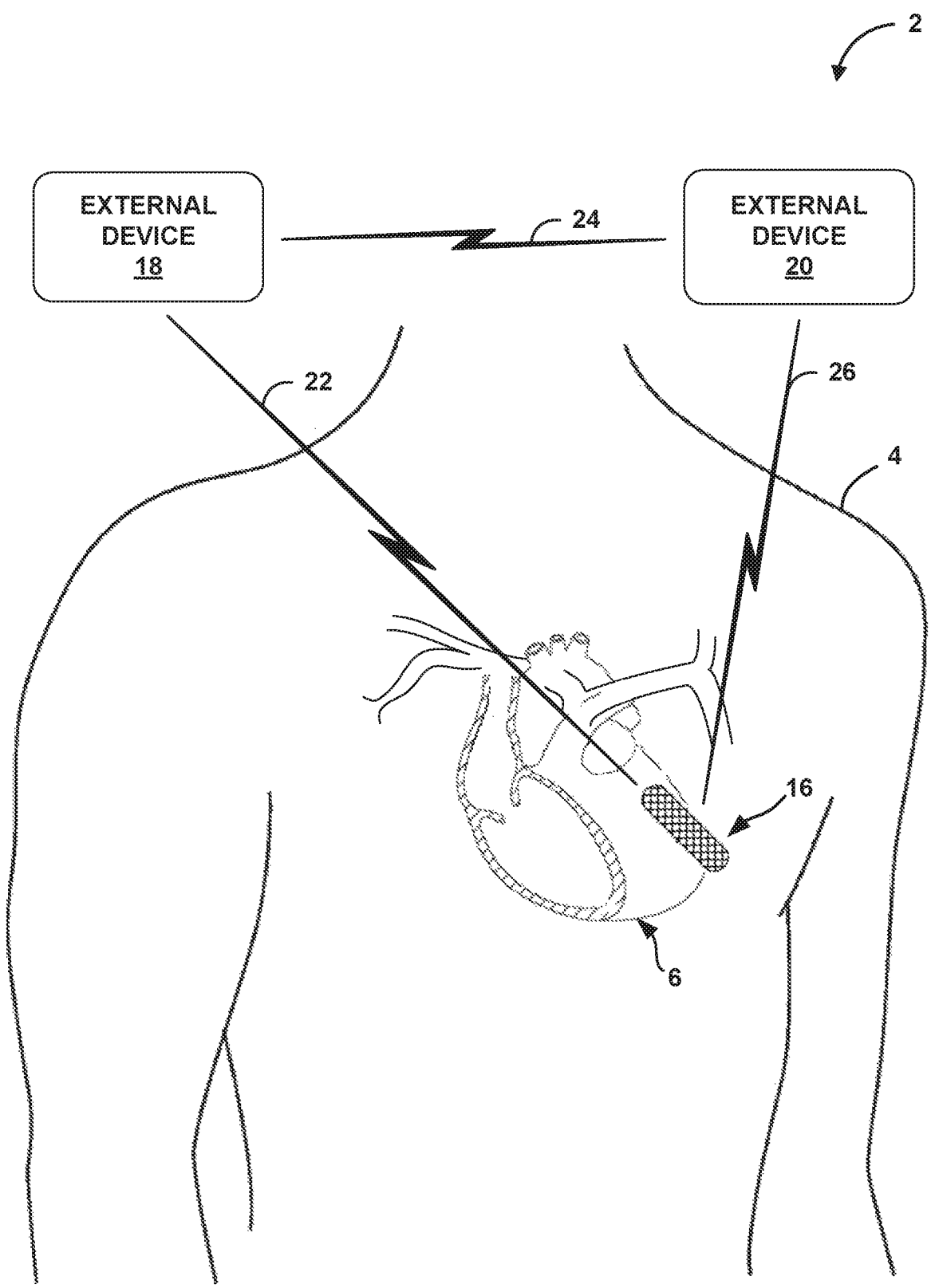
FIG. 1 illustrates the environment of an example medical device system in conjunction with a patient and a heart of the patient, in accordance with one or more techniques of this disclosure.

This disclosure describes techniques for establishing a secure connection between two or more devices. In some examples, a secure link is established between at least one implantable medical device (IMD) and at least one external device. An external device may be used to, for example, transmit a signal to the IMD in order to initiate an encryption key generation process which would enable at least one external device to exchange encrypted data with the IMD. However, the techniques of this disclosure are not limited to implantable devices or medical devices. The techniques may be used to establish a secure link between any two or more devices that can communicate with each other.

In some examples, an IMD records one or more physiological signals of a patient, where the one or more physiological signals may be indicative of a medical condition. The IMD may use any combination of electrodes, chemical sensors, temperature sensors, or other sensors to sense the physiological signals and store data indicative of the physiological signals in a memory. In some examples, the IMD delivers therapy, such as cardiac pacing or anti-tachyarrhythmia shocks, and store data indicative of the therapy delivered. In some examples, the IMD stores data regarding the status and performance of the IMD and components thereof, and operational parameters that control the functioning of the IMD, e.g., for sensing and/or delivering therapy.

Since the IMD is implanted within the patient, in some cases, the IMD may wirelessly communicate with an external device, e.g., to transmit at least some of the data to an external device for analysis by a clinician. Additionally, a user (e.g., the patient or the clinician) may provide user input to an external device to control the IMD. The external device may in turn transmit instructions to the IMD based on the user input. Since information exchanged between the IMD and the external device may be sensitive and is communicated wirelessly, it may be beneficial to exchange data with the IMD using a secure link such as an encrypted link.

To transfer data using an encrypted link, a plurality of different encryption algorithms may be used. Such algorithms may include Rivest-Shamir-Adleman (RSA), advanced encryption standard (AES), elliptic curve integrated encryption scheme (ECIES), data encryption standard (DES), twofish, threefish, or key exchange method, as examples. While different encryption algorithms vary in their methods of encoding and decoding data, most encryption algorithms rely on encryption keys for the encoding and the decoding process. For example, a first device may encode a message using a first encryption key and transmit the encoded message to a second device. The second device may decode the message using a second encryption key, where the second encryption key corresponds to the first encryption key. Consequently, if the external device does not possess an encryption key corresponding to an encryption key of the IMD, then the external device may be unable to securely communicate with the IMD.

The external device is configured to initiate a process to generate a set of encryption keys (e.g., "session" keys) which allow one or more external devices to communicate with the implantable medical device. The external device may send an initial signal to the IMD to begin the process of creating the set of encryption keys. The initial signal may also, in some cases, "wake up" the IMD for a communication session (e.g., cause the IMD to supply a greater amount of power to communication circuitry of the IMD). The initial signal may have a short transmission range (e.g., less than about 20 centimeters (cm)), decreasing a probability that a fraudulent device would be able to imitate the initial signal to start the key creation process. In some cases, the external device or a portion thereof used to facilitate communication with the IMD must be placed directly across the patient's skin from the IMD for the initial signal transmission to be successful. After the IMD receives the initial signal, the external device and the IMD may generate the set of encryption keys and establish the secure link.

FIG. 1 illustrates the environment of an example medical device system 2 in conjunction with a patient 4 and a heart 6 of patient 4, in accordance with one or more techniques of this disclosure. The example techniques may be used with an IMD 16, which may be in wireless communication with at least one of external device 18 and external device 20. In some examples, IMD 16 is implanted outside of a thoracic cavity of patient 4 (e.g., subcutaneously in the pectoral location illustrated in FIG. 1). IMD 16 may be positioned near the sternum near or just below the level of heart 6, e.g., at least partially within the cardiac silhouette. In some examples, IMD 16 takes the form of a LINQ™ Insertable Cardiac Monitor (ICM), available from Medtronic plc, of Dublin, Ireland.

Clinicians sometimes diagnose patients with cardiac conditions based on one or more observed physiological signals collected by physiological sensors, such as electrocardiogram (ECG) electrodes, electrogram (EGM) electrodes, chemical sensors, or temperature sensors. In some cases, clinicians apply non-invasive sensors to patients in order to sense one or more physiological signals while a patent is in a clinic for a medical appointment. However, in some examples, physiological markers (e.g., irregular heartbeats) of a cardiac condition are rare. As such, in these examples, a clinician may be unable to observe the physiological markers needed to diagnose a patient with a heart condition while monitoring one or more physiological signals of the patient during a medical appointment. In the example illustrated in FIG. 1, IMD 16 is implanted within patient 4 to continuously record one or more physiological signals of patient 4 over an extended period of time.

In some examples, IMD 16 includes a plurality of electrodes. The plurality of electrodes are configured to detect signals that enable processing circuitry of IMD 16 to determine current values of additional parameters associated with the cardiac and/or lung functions of patient 4. In some examples, the plurality of electrodes of IMD 16 are configured to detect a signal indicative of an electric potential of the tissue surrounding the IMD 16. Moreover, IMD 16 may additionally or alternatively include one or more accelerometers, temperature sensors, chemical sensors, light sensors, pressure sensors, in some examples. Such sensors may detect one or more physiological parameters indicative of a patient condition.

External device 18 may include a housing which encloses processing circuitry electrically coupled to communication circuitry, a memory, and a user interface. In some examples, external device 18 is physically separate from external device 20. The user interface of external device 18 may include, for example, at least one button. Additionally, or alternatively, the user interface of external device 18 may include any other device, sensor, or medium configured for accepting user input. In some examples, the user interface of external device 18 enables a user to initiate one or more techniques of this disclosure which establish a secure (e.g., encrypted) link with IMD 16 for a period of time. Although external device 18 may be physically separated from external device 20, external device 18 is configured to, for example, establish a secure connection between external device 20 and IMD 16. In some cases, external device 18 may act as an intermediary for communication between external device 20 and IMD 16, e.g., during a secure communication session. In other cases, external device 18 may establish a secure link with IMD 16 without including any additional devices (e.g., external device 20).

In some examples, external device 18 is configured for handheld use. In fact, a user may, in some cases, be able to fit external device 18 in the palm of a single hand while interacting with the user interface using at least one finger. In addition to being configured for handheld use, external device 18 may be configured to transmit signals via the communication circuitry according to at least one communication protocol. One communication protocol, for example, may enable external device 18 to send signals to IMD 16 over a short range (e.g., less than about 20 cm). For example, external device 18 may communicate via near-field communication technologies (e.g., inductive coupling, Near-field Communication (NFC) or other communication technologies operable at ranges less than 10-20 cm). Another example communication protocol may enable IMD 16, external device 18, and external device 20 to communicate over a relatively longer range. For example, external device 18 may communicate using far-field communication technologies (e.g., radiofrequency (RF) telemetry according to the 802.11 or Bluetooth® specification sets, or other communication technologies operable at ranges greater than near-field communication technologies).

External device 20 is configured to wirelessly communicate with IMD 16 as needed to provide or retrieve information. In some examples, external device 20 acts as an external programming device, e.g., medical device programmer, for IMD 16. External device 20 is an external computing device that a user, e.g., the clinician and/or patient 4, may use to communicate with IMD 16. For example, external device 20 may be a clinician programmer that the clinician uses to communicate with IMD 16 and update one or more settings of IMD 16. Additionally, or alternatively, external device 20 may be a patient programmer that allows patient 4 to control certain operations of IMD 16 and/or view and modify one or more operational parameter values of IMD 16. The clinician programmer may include more programming features than the patient programmer. In other words, more complex or sensitive tasks may only be allowed by the clinician programmer to prevent an untrained patient from making undesired changes to IMD 16.

External device 20 may be a hand-held computing device with a display viewable by the user and an interface for providing input to external device 20 (i.e., a user input mechanism). For example, external device 20 may include a small display screen (e.g., a liquid crystal display (LCD) or a light emitting diode (LED) display) that presents information to the user. In addition, external device 20 may include a touch screen display, keypad, buttons, a peripheral pointing device, voice activation, or another input mechanism that allows the user to navigate through the user interface of external device 20 and provide input. If external device 20 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 20 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device. In some examples, a wireless adapter coupled to the computing device enables external device 18 to establish a secure link between the computing device and IMD 16.

When external device 20 is configured for use by the clinician, external device 20 may be used to transmit instructions to IMD 16. Example instructions may include requests to set electrode combinations for sensing and any other information that may be useful for programming into IMD 16. The clinician may also configure and store operational parameters for IMD 16 within IMD 16 with the aid of external device 20. In some examples, external device 20 assists the clinician in the configuration of IMD 16 by providing a system for identifying potentially beneficial operational parameter values.

Whether external device 20 is configured for clinician or patient use, external device 20 is configured to communicate with IMD 16 and, optionally, another computing device (e.g., external device 18), via wireless communication. External device 20, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

In general, IMD 16, external device 18, and external device 20 may exchange information using at least one communication protocol. Communication protocols define sets of rules that define one or more aspects of data exchange between two or more entities of a network. In some examples, communication protocols are stored as lists of computer-readable instructions and communication protocols may be executed by any combination of hardware (e.g., physical circuitry) and software. An organization, such as a medical device manufacturer, may create its own communication protocols, license communication protocols from a third party, use open source communication protocols, or perform any combination thereof. In some examples, a communication protocol includes security provisions, such as password requirements and data encryption in order to secure the transfer of data between two or more devices in a network.

IMD 16 collects sensitive physiological data from patient 4. Additionally, IMD 16 may receive data indicative of instructions from external device 20, where the instructions cause IMD 16 to, as examples, update one or more settings, change one or more parameters, output data, or delete data. Consequently, communications (e.g., information or data) transmitted between external device 20 and IMD 16 may be encrypted to secure the communications from unauthenticated users and prevent external device 20 and IMD 16 from becoming compromised. For instance, communications transmitted between external device 20 and IMD 16 using a far-field communication protocol may be encrypted using a link key that is generated based on public encryption keys of external device 20 and IMD 16. An encryption key may define a string of characters that is used to transform data into an encrypted form, decode encrypted data, or any combination thereof. As such, a first device may be unable to securely communicate with a second device if any one of the first device and the second device does not possess a respective encryption key associated with a secure link between the first device and the second device.

In some cases, external device 20 does not have access to a public encryption key associated with IMD 16 and is thus unable to transmit encrypted data to IMD 16. In these cases, techniques for establishing a secure link between external device 20 and IMD 16 may be beneficial. In some example techniques of this disclosure, external device 18 is configured to establish the secure link by, in part, transmitting a short-range signal to IMD 16.

Any combination of IMD 16, external device 18, and external device 20 may exchange information and data with each other. As illustrated in FIG. 1, IMD 16 is configured to communicate with external device 18 over communication link 22, External device 18 is configured to communicate with external device 20 over communication link 24, and IMD 16 is configured to communicate with external device 20 over communication link 26. In some examples, each of communication links 22, 24, and 26 include any combination of secure channels (e.g., encrypted channels) and insecure channels (non-encrypted channels). Put another way, each of communication links 22, 24, and 26 represent all communications between the respective pairs of devices.

In one example, external device 18 is configured to transmit non-encrypted data to IMD 16 over communication link 22 and external device 18 is further configured to transmit encrypted data to IMD 16 over communication link 22. In some examples, the communication circuitry of external device 18 is configured for wireless communication according to a first protocol and a second protocol, where the first protocol is different from the second protocol. For example, the first protocol defines a first range and the second protocol defines a second range. In other words, a maximum distance in which a signal may be transmitted according to the first protocol is different from a maximum distance in which a signal may be transmitted according to the second protocol. In some examples, the second range is greater than the first range. However, in other examples, the second range is less than or equal to the first range.

The processing circuitry of external device 18 may transmit, via the communication circuitry, a first signal to IMD 16 according to the first protocol. In some examples, the first protocol includes any communication protocol which uses magnetic induction communication, RF communication, or tissue conductance communication (TCC) via tissue of the patient. In some examples, the first range (e.g., the maximum range of the first signal) is less than about 20 cm. In other examples, the first range is less than about 10 cm.

In some examples, the first signal is defined by an electromagnetic waveform which acts as a "wake-up" signal for IMD 16. Signal reception circuitry (not illustrated in FIG. 1) of IMD 16 may receive the first signal. The signal reception circuitry may be configured for sensing electromagnetic waveforms. After receiving the first signal, the signal reception circuitry may send data indicative of the first signal to the processing circuitry of FIG. 1. The first signal may, in some cases, cause the processing circuitry of IMD 16 to transition at least some circuitry, such as communication circuitry of IMD 16, from a relatively lower energy consumption mode into a relatively higher energy consumption mode in which communication with one or more external devices occurs. Since IMD 16 is powered by a power source which, in some examples, has a limited lifespan, it may be beneficial to power the communication circuitry only when necessary for the functioning of IMD 16. As such, IMD 16 may use the communication circuitry only after receiving the "wake up" signal, such as the first signal transmitted by external device 18. For example, IMD 16 may transition the communication circuitry from being in an off state in which the communication circuitry is not transmitting or receiving to being in an on state during which the communication circuitry is capable of transmitting and receiving. The signal reception circuitry of IMD 16 may, in some cases, be separate from the communication circuitry of IMD 16. In other cases, the signal reception circuitry may be a component of, or a part of the communication circuitry of IMD 16. In either case, the signal reception circuitry is configured to sense the first signal which is transmitted from external device 18 to IMD 16. In some examples, the signal reception circuitry may be configured for detecting TCC signals, where the first signal includes a TCC signal.

In some examples, the communication circuitry of IMD 16 periodically emits a sequence of advertisements according to the second protocol. Advertisements emitted by IMD 16 may broadcast to other devices the proximity and/or readiness of IMD 16 to communicate. IMD 16 may emit advertisements at a first advertisement rate prior to receiving the "wake up" signal and transition to a second, faster advertisement rate after receiving the "wake up" signal. In one example, the first advertisement rate may be greater than twenty advertisements per hour and less than sixty advertisements per hour. Put another way, consecutive advertisements of the sequence of advertisements may be separated by a period of time lasting greater than or equal to one minute and less than or equal to three minutes. In some examples, the first advertisement rate may be insufficient for establishing a secure link with another device (e.g., external devices 18, 20) in a desired amount of time. In response to detecting the first signal, IMD 16 increases the rate at which the communication circuitry of IMD 16 transmits advertisements to a second rate. The increased second advertisement rate increases the power consumption of IMD 16, e.g., of the communication circuitry of IMD 16. The second advertisement rate may be high enough to enable IMD 16 to establish a secure link with external devices 18, 20 within a desired amount of time, e.g., seconds instead of minutes. In some examples, the second advertisement rate is greater than one advertisement per second. As such, the second advertisement rate is significantly higher than the first advertisement rate, and the communication circuitry of IMD 16 consumes more power when operating at the second advertisement rate than when the communication circuitry is operating at the first advertisement rate. In some examples, after receiving the first signal, IMD 16 operates at the second advertisement rate for a period of time, e.g., lasting up to thirty seconds, so as to not operate in the increased higher power consumption mode for too long. Since, in some cases, IMD 16 increases the advertisement rate from the first advertisement rate to the second advertisement rate only after receiving the first signal, IMD 16 may decrease a total amount of power required for establishing a secure link between IMD 16 and external devices 18, 20. This may increase a life span of the power source which provides power to the components of IMD 16.

The processing circuitry of external device 18 may be configured to cause external device 18 to generate the first signal. In one example, the first signal includes a plurality of primary portions defining a first frequency value and a first duration. Additionally, the first signal includes a plurality of secondary portions defining a second frequency value and a second duration. The plurality of primary portions and the plurality of secondary portions are interleaved such that one primary portion occurs between two consecutive secondary portions and one secondary portion occurs between two consecutive primary portions.

In some examples, external device 18 is configured to transmit the first signal in response to a user input to the user interface of external device 18 (e.g., a press of the button). Alternatively, external device 18 may be configured to transmit the first signal in response to receiving data indicative of an instruction from external device 20. In some examples, external device 18 transmits the first signal for a fixed amount of time lasting about 255 milliseconds (ms). Alternatively, in other examples, external device 18 transmits the first signal for a fixed amount of time lasting greater than or less than about 255 milliseconds. In other examples, external device 18 is configured to transmit the first signal for a period of time lasting as long as a user is pressing the button defining the user interface.

IMD 16 is configured to receive the first signal. Although external device 18 transmits the first signal according to the first protocol, IMD 16 is not configured to, in some examples, communicate (including transmitting and receiving information) according to the first protocol. However, the signal reception circuitry (not illustrated in FIG. 1) of IMD 16 is configured to detect electromagnetic field variations, wherein the electromagnetic variations may be induced by TCC signals, magnetic induction signals, RF signals, or other kinds of signals. As such, IMD 16 is configured to detect the first signal, since the first signal causes electromagnetic field variations within the first range of external device 18. In fact, IMD 16 may be configured to detect one or more parameters of the first signal based on the electromagnetic field variations, such as the first frequency value, the second frequency value, the first duration, the second duration, and the total duration.

In some examples, IMD 16 is configured to cross-reference values of the one or more detected parameters of the first signal with one or more baseline values of the detected parameters, where the one or more baseline values are stored in a memory of IMD 16. Subsequently, IMD 16 is configured to determine if the first signal matches an expected first signal associated with external device 18. In response to determining that external device 18 transmitted the first signal, IMD 16 is configured to transmit, via the communication circuitry of IMD 16, a second signal to the external device according to the second protocol. The second signal may include a set of advertisements for establishing the secure link. The second protocol, which is different than the first protocol, may be communication protocol known to both IMD 16 and external device 18. In some examples, the second protocol includes a Bluetooth® protocol such as a Bluetooth® Low Energy (BTLE) protocol.

A device (e.g., IMD 16, external device 18, or external device 20) may be configured to transmit signals according to the second protocol while the device is operating in a reduced power mode or a normal power mode. In some examples, when transmitting signals according to the second protocol and while operating in the normal power mode, the device may transmit signals at 0 decibels with reference to one milliwatt (dBm). Additionally, in some examples, when transmitting signals according to the second protocol and while operating in the reduced power mode, the device may transmit signals at −20 dBm. In other words, a power magnitude of signals transmitted while the device is operating in the reduced power mode may be decreased a hundredfold from a power magnitude of signals transmitted while the device is operating in the normal power mode. In other examples, when transmitting signals according to the second protocol and while operating in the reduced power mode, the device may transmit signals within a range from −50 dBm to −10 dBm.

The second signal transmitted by IMD 16 may include a set of advertisements transmitted at the second advertisement rate. In some examples, prior to transmitting the second signal at the second advertisement rate in response to receiving the first signal, IMD 16 may transmit advertisements at the first advertisement rate, where the first advertisement rate is less than the second advertising rate. In other examples, prior to transmitting the second signal at the second advertisement rate, the communication circuitry of IMD 16 is powered off and IMD 16 does not transmit advertisements. In such examples, the second advertisement rate may be the only rate in which IMD 16 transmits advertisements. External device 18 is configured to receive the second signal including the set of advertisements. Subsequently, in some examples, external device 18 is configured to generate a first set of random data. In other examples, external device 18 may transmit, via communication link 24, a notification to external device 20 that the second signal is received and external device 20 generates the first set of random data. External devices 18, 20 may transmit the first set of random data to IMD 16, and in response to receiving the first set of random data, IMD 16 may generate a second set of random data. In some examples, the first set of random data and the second set of random data each include a 64-bit integer.

IMD 16 may be configured to store an encrypted form of a first encryption key and a non-encrypted form of the first encryption key. The first encryption key may, in some cases, be a "device key" that is created and stored in IMD 16 at a time when IMD 16 is manufactured. In some examples, the encrypted form of the first encryption key is encrypted using a public key of the ECIES security algorithm. After generating the second set of random data, IMD 16 is configured to transmit the second set of random data, a challenge, and the encrypted form of the first encryption key to external device 18. IMD 16 may transmit the second set of random data, the challenge, and the encrypted form of the first encryption key according to the second protocol, but with reduced power relative to subsequent communication according to the second protocol. In some examples, e.g., where the IMD 16 uses reduced power, IMD 16 transmits the second set of random data, the challenge, and the encrypted form of the first encryption key having a power magnitude of less than about 150 nanowatts (nW). To improve security by limiting the range in which a device is configured to intercept the second set of random data, the challenge, and the encrypted form of the first encryption key, it may be desirable to transmit with reduced power, e.g., defining a maximum range of about 1 meter.

The challenge includes, in some cases, a non-encrypted 64-bit integer. IMD 16 may store the challenge in a memory as a template challenge for future verification. Additionally, in some examples, IMD 16 is configured to calculate a second encryption key based on the first set of random data, the second set of random data, and the non-encrypted form of the first encryption key.

External device 18 may receive the second set of random data, the challenge, and the encrypted form of the first encryption key. In some examples, external device 18 relays the second set of random data, the challenge, and the encrypted form of the first encryption key to external device 20 via communication link 24. Each of IMD 16, external device 18, and external device 20 are configured to commit the first set of random data and the second set of random data to respective memories. Any combination of external device 18 and external device 20 are configured to decrypt the first encryption key using, in some examples, a private key of the ECIS security algorithm. As such, external devices 18, 20 are configured to obtain the non-encrypted form of the first encryption key. External devices 18, 20 may calculate the second encryption key based on the first set of random data, the second set of random data, and the non-encrypted form of the first encryption key. Thus, IMD 16 and external devices 18, 20 may each calculate the second configuration independently of each other. The independent generation of the second encryption key ensures that the second encryption key does not need to be wirelessly transmitted between IMD 16 and external devices 18, 20 therefore decreasing a probability that the second encryption key is intercepted or otherwise compromised.

In some examples, external devices 18, 20 are configured to encrypt, using the second encryption key, the challenge received from IMD 16. External device 18 may transmit the encrypted challenge to IMD 16. Since IMD 16 is configured to calculate the second encryption key independently from external devices 18, 20, IMD 16 may decrypt the encrypted challenge using the second encryption key. To verify the encrypted challenge transmitted by external device 18 and decrypted by IMD 16, IMD 16 is configured to cross-reference the challenge received from external device 18 with the template challenge, where the template challenge corresponds to the challenge originally sent to external device 18. In other words, transmitting the challenge to external device 18 and receiving the encrypted challenge from external device 18 enables IMD 16 to verify that external devices 18, 20 possess the second encryption key.

IMD 16 is configured to transmit a verification signal to external device 18 which establishes a secure link between IMD 16 and external devices 18, 20. In some examples, communications transmitted over the secure link are at the normal power mode of the second protocol. External device 18 is configured to receive the verification signal, and in some cases add external device 20 to the secure link, thus enabling both of external device 18 and external device 20 to communicate with IMD 16 over the secure link. In one example, external device 18 communicates with external device 20 over a secure channel of communication link 24 and also communicates with IMD 16 over a secure channel of communication link 22. As such, in this example, external device 18 acts as an intermediary between external device 20 and IMD 16, therefore establishing an indirect secure link between external device 20 and IMD 16.

In some cases, it may be desirable to terminate a secure link between any combination of IMD 16, external device 18, and external device 20. A secure link between external device 20 and IMD 16 may be terminated if any one of IMD 16, external device 18, or external device 20 outputs an instruction to terminate the secure link. Additionally, in examples where external device 18 acts as an intermediary between external device 20 and IMD 16, if external device 18 exits a range required to communicate with either IMD 16 or external device 20, the secure link is terminated. In some examples, after a secure link with IMD 16 is established by external device 18, a time window is started, where the time window is set to expire after a predetermined amount of time. If the time window expires before the secure link is terminated, IMD 16 may terminate the secure link. In some examples, the predetermined amount of time is about one hour.

In some examples, any combination of IMD 16, external device 18, external device 20, or other external devices (not illustrated in FIG. 1) create a set of additional encryption keys using the second encryption key. Each additional encryption key of the set of additional encryption keys may enable the encryption and decryption of a particular class of data. For example, one additional encryption key may enable the encryption and decryption of physiological data stored in IMD 16.

In some examples, a power magnitude of transmissions made over the secure link is greater than a power magnitude of the second set of random data, the challenge, and the encrypted form of the first encryption key sent by IMD 16 to external device 18 as part of the key generation process.

Although external device 18 and external device 20 are illustrated in FIG. 1 as being separate devices, in some examples (not illustrated), a single external device performs the functions of both external device 18 and external device 20.

Although in one example IMD 16 takes the form of an ICM, in other examples, IMD 16 takes the form of any combination of implantable cardioverter defibrillators (ICDs), pacemakers, cardiac resynchronization therapy devices (CRT-Ds), spinal cord stimulation (SCS) devices, deep brain stimulation (DBS) devices, left ventricular assist devices (LVADs), implantable sensors, orthopedic devices, or drug pumps, as examples. Moreover, techniques of this disclosure may be used to establish secure connections with any one of the aforementioned IMDs. Moreover, techniques described in this disclosure may be applied to establish a secure link between two or more devices, where none of the two or more devices are implantable devices. Additionally, in some examples, techniques described in this disclosure may be applied to establish a secure link between two or more devices, where none of the two or more devices are medical devices.

Figure 2:
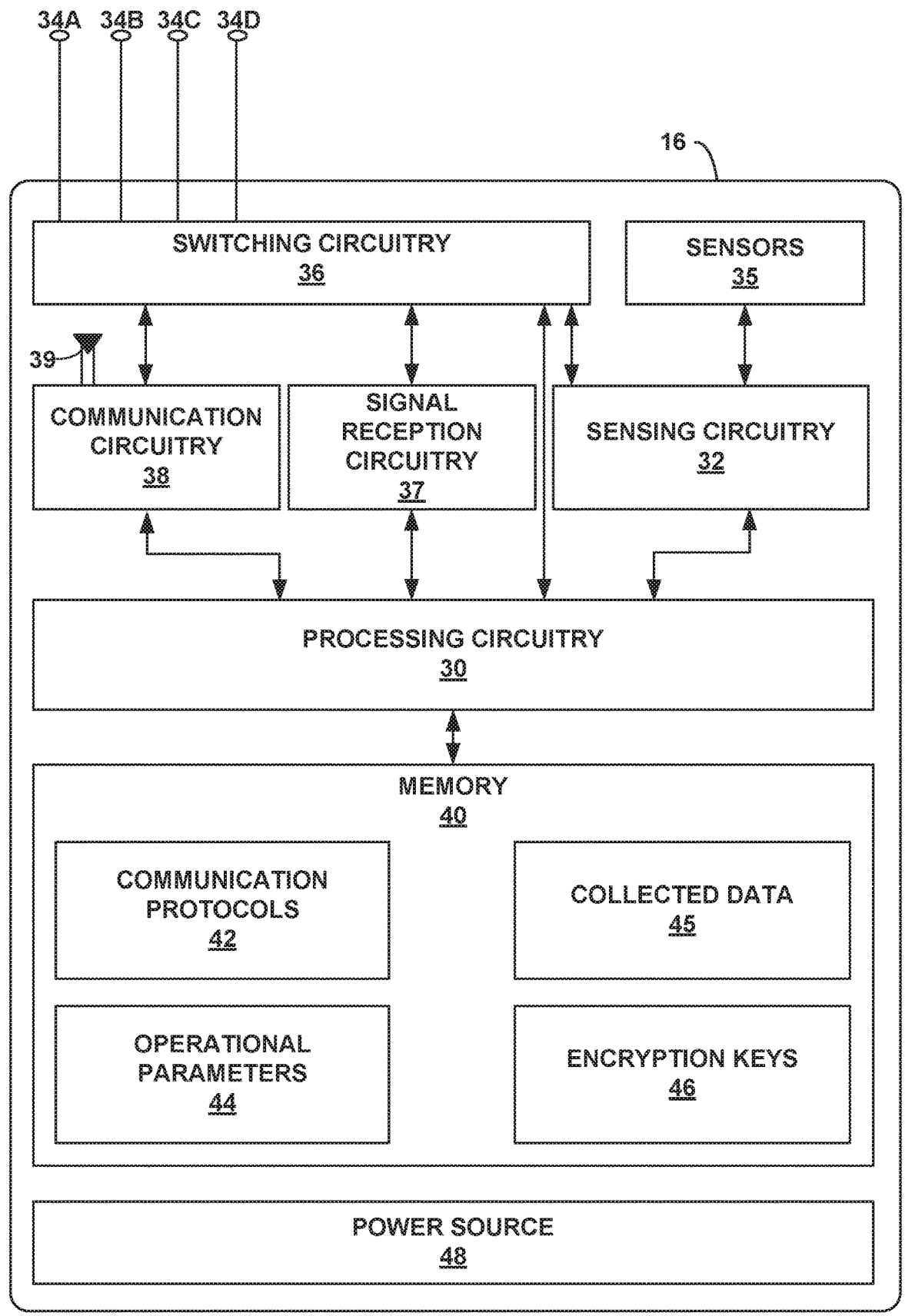
FIG. 2 is a block diagram illustrating an example configuration of components of an implantable medical device (IMD), in accordance with one or more techniques of this disclosure.

FIG. 2 is a block diagram illustrating an example configuration of components of IMD 16 in accordance with one or more techniques of this disclosure. In the example of FIG. 2, IMD 16 includes processing circuitry 30, sensing circuitry 32, electrodes 34A-34D (collectively, "electrodes 34"), sensors 35, switching circuitry 36, signal reception circuitry 37, communication circuitry 38, antenna 39, memory 40, and power source 48. Memory 40 is configured to store communication protocols 42, operational parameters 44, collected data 45, and encryption keys 46.

Processing circuitry 30, in one example, may include one or more processors that are configured to implement functionality and/or process instructions for execution within IMD 16. For example, processing circuitry 30 may be capable of processing instructions stored in memory 40. Processing circuitry 30 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 30 may include any suitable structure, whether in hardware, software, firmware, or any combination thereof, to perform the functions ascribed herein to processing circuitry 30.

Sensing circuitry 32 monitors electrical cardiac signals from any combination of electrodes 34A-34D (collectively, "electrodes 34"). In some examples, sensing circuitry 32 may include one or more amplifiers, filters, and analog-to-digital converters. For example, sensing circuitry 32 may include one or more detection channels, each of which may include an amplifier. The detection channels may be used to sense cardiac signals, such as a cardiac EGM. Some detection channels may detect events, such as R-waves, P-waves, and T-waves and provide indications of the occurrences of such events to processing circuitry 30. Additionally, or alternatively, some channels may detect cardiac EGM signals from a particular combination of electrodes 34. One or more other detection channels may provide signals to an analog-to-digital converter, for conversion into a digital signal for processing, analysis, storage, or output by processing circuitry 30.

Each detection channel of sensing circuitry 32 may include a filter configured to pass a custom range of frequency values. For example, sensing circuitry 32 may include one or more narrow band channels, each of which may include a narrow band filtered sense-amplifier. Additionally, or alternatively, sensing circuitry 32 may include one or more wide band channels, each of which include an amplifier with a relatively wider pass band than the narrow band channels. Signals sensed by the narrow band channels and the wide band channels of sensing circuitry 32 may be converted to multi-bit digital signals by an analog-to-digital converter (ADC) provided by, for example, sensing circuitry 32 or processing circuitry 30. In some examples, processing circuitry 30 analyzes the digitized version of signals from sensing circuitry 32. In other examples, processing circuitry 30 stores the digitized versions of the signals in memory 40 (e.g., as collected data 45), outputs the digitized versions of the signals via communication circuitry 38, or any combination thereof.

Processing circuitry 30 may use switching circuitry 36 to select, e.g., via a data/address bus, which of electrodes 34 to use for sensing cardiac signals. Switching circuitry 36 may include a switch array, switch matrix, multiplexer, or any other type of switching device suitable to selectively couple energy to selected electrodes.

In some examples, sensing circuitry 32 is electrically coupled to sensors 35. Sensors 35 may include any combination of accelerometers, temperature sensors, chemical sensors, light sensors, and pressure sensors. Sensors 35 may, for example, sense one or more physiological parameters indicative of a heart condition. Additionally, or alternatively, an accelerometer of sensors 35 may sense data indicative of at least one of patient posture and patient activity.

Signal reception circuitry 37 may include hardware, firmware, software or any combination thereof for receiving signals from another device, such as external device 18 or external device 20. For example, signal reception circuitry 37 may be configured to detect electromagnetic variations indicative of a signal. In some cases, the signal may include a TCC signal. In such cases, signal reception circuitry 37 may include circuitry configured for detecting electromagnetic field variations indicative of the TCC signal. Signal reception circuitry 37 may be powered by power source 48, "listening" for signals from external device 18 or external device 20. In other examples, power source 48 may power signal reception circuitry 37 every 250 ms for a period of time, where the period of time lasts for greater than 0.1 ms and less than 50 ms. In this way, signal reception circuitry 37 may alternate between an "off" state and an "on" state, where signal reception circuitry 37 is configured to detect signals while signal reception circuitry 37 is being powered by power source 48 during the on state.

Communication circuitry 38 may include any suitable hardware, firmware, software or any combination thereof for communicating with another device, such as external device 18 or external device 20. Under the control of processing circuitry 30, communication circuitry 38 may receive downlink telemetry from, as well as send uplink telemetry to, external device 18, external device 20, or another device with the aid of an internal or external antenna, e.g., antenna 39. In addition, processing circuitry 30 may communicate with a networked computing device via an external device (e.g., external device 18) and a computer network, such as the Medtronic CareLink® Network developed by Medtronic, plc, of Dublin, Ireland. Communication circuitry 38 may include any combination of a Bluetooth® radio, an electronic oscillator, frequency modulation circuitry, frequency demodulation circuitry, amplifier circuitry, and power switches such as a metal-oxide-semiconductor field-effect transistors (MOSFET), a bipolar junction transistor (BJT), an insulated-gate bipolar transistor (IGBT), a junction field effect transistor (JFET), or another element that uses voltage for its control. In examples in which IMD 16 receives the first signal from external device 18 via tissue conductance communication, communication circuitry 38 may receive the first signal via one or more of electrodes 34. Signal reception circuitry 37 may, in some cases, be separate from communication circuitry 38. In other cases, signal reception circuitry 37 may be a component of, or a part of communication circuitry 38.

Memory 40 may be configured to store information within IMD 16 during operation. Memory 40 may include a computer-readable storage medium or computer-readable storage device. In some examples, memory 40 includes one or more of a short-term memory or a long-term memory. Memory 40 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, memory 40 is used to store data indicative of instructions for execution by processing circuitry 30.

In some examples, memory 40 is configured to store one or more communication protocols 42. Each protocol of communication protocols 42 may define a set of rules that govern one or more aspects of data exchange between IMD 16 and other devices (e.g., external device 18 and external device 20. In some examples, communication protocols 42 are stored as lists of computer-readable instructions and communication protocols may be executed by any combination of hardware (e.g., processing circuitry 30) and software. In some examples, communication protocols 42 includes a Bluetooth® protocol such as a BTLE protocol. In some examples, communication protocols 42 exclusively include the Bluetooth® protocol. Alternatively, in other examples, communication protocols 42 may include any combination of Bluetooth® protocols, protocols developed by the manufacturer of IMD 16, and protocols licensed from a third-party developer.

In some examples, memory 40 is configured to store operational parameters 44. Operational parameters 44 may govern aspects of the operation of IMD 16. For example, operational parameters 44 may include combinations of electrodes 34 and sensors 35 for sensing physiological signals of patient 4. Additionally, or alternatively, operational parameters 44 may include a sampling rate for sampling analog signals sensed by electrodes 34 and sensors 35. Operational parameters 44 may be updated based on instructions received from an external device (e.g., external device 20) via communication circuitry 38. In some examples, processing circuitry 30 of IMD 16 updates operational parameters 44 only if instructions to update operational parameters 44 are received over a secure link.

In some examples, memory 40 is configured to store collected data 45. Collected data 45 may include any data sensed, processed, or analyzed by IMD 16, where the data is acquired via any combination of electrodes 34, sensors 35, signal reception circuitry 37 and communication circuitry 38. In some examples, collected data 45 includes a cardiac EGM recording sensed by sensing circuitry 32 via electrodes 34 and processed by processing circuitry 30. Additionally, or alternatively, collected data 45 may include data acquired by one or more chemical sensors of sensors 35, where the data is indicative of a presence of or a possibility of at least one heart condition (e.g., heart failure). Thus, in general, collected data 45 may represent physiological signals acquired from patient 4 over a period of time. In some examples, the period of time lasts for greater than 12 hours and less than 72 hours. In other examples, the period of time lasts for up to one month. Put another way, IMD 16 is configured to continuously monitor physiological signals over the period of time and store at least some of these physiological signals in memory 40 as collected data 45.

Collected data 45 may include sensitive information. Thus, it may be desirable to restrict the access of collected data 45 to patient 4 and clinicians responsible for the medical care of patient 4. For at least these reasons, if a portion of collected data 45 is transmitted from IMD 16 to another device (e.g., external device 18 or external device 20), processing circuitry 30 may transmit the portion of collected data 45 over a secure link (e.g., an encrypted link). To transmit data over the secure link, processing circuitry 30 may encode data using one or more of encryption keys 46 stored in memory 40. By the same token, processing circuitry may decode encrypted data received by IMD 16 from other devices using encryption keys 46. At least one of encryption keys 46 may include an advanced encryption standard (AES) key which defines a 128-bit integer. In some examples, to improve security measures, IMD 16 only transmits collected data 45 via encrypted communication links. Additionally, in some examples, encryption keys 46 include an encrypted form of a device key and a non-encrypted form of the device key. The device key may represent a key that is stored within memory 40 at a time that IMD 16 is manufactured. The encrypted form of the device key may be encrypted using a public key of the ECIES security algorithm.

Another device (e.g., external device 18) may attempt to establish a secure link with IMD 16. For example, signal reception circuitry 37 of IMD 16 may receive a first signal from external device 18. The first signal, in some examples, causes processing circuitry 30 to trigger communication circuitry 38 to begin transmitting advertisements. In other examples, the first signal causes processing circuitry 30 to increase a rate in which communication circuitry 38 transmits advertisements. In examples where the first signal causes processing circuitry 30 to trigger communication circuitry 38 to begin transmitting advertisements, communication circuitry 38 may be off prior to signal reception circuitry 37 receiving the first signal. In examples where the first signal causes processing circuitry 30 to increase the advertisement rate, communication circuitry 38 may transmit advertisements at a first advertisement rate prior to IMD 16 receiving the first signal and transmit advertisements at a second advertisement rate after IMD 16 receives the first signal, where the second advertisement rate is greater than the first advertisement rate. When transmitting advertisements, communication circuitry 38 may be powered by power source 48 during the transmission of each advertisement. Additionally, communication circuitry 38 may be powered for a period of time following each advertisement in order to listen for a response to the respective advertisement. In this manner, increasing the advertisement rate may cause a rate in which power is drained from power source 48 to increase.

Communication protocols 42 may include one or more protocols and may enable IMD 16 to communicate according to a Bluetooth® protocol, as an example. However, in some examples, the first signal is transmitted according to a communication protocol other than the Bluetooth® protocol, where the communication protocol is unknown to IMD 16 (e.g., the communication protocol is not included in communication protocols 42 stored by memory 40. Even if the communication protocol of the first signal is not known to IMD 16, signal reception circuitry 37 may, for example, sense the first signal by detecting electromagnetic field variations associated with the first signal. Moreover, processing circuitry 30 may process the first signal to determine one or more parameters of the first signal such as frequency components or signal duration. Based comparing the one or more parameters of the detected signal with one or more known parameters stored by memory 40, processing circuitry 30 may verify that the first signal was transmitted by a trusted device (e.g., external device 18).

IMD 16 may be configured to transmit a second signal to external device 18 via communication circuitry 38 according to one of communication protocols 42. As such, the second signal is transmitted from IMD 16 to external device 18 according to a different communication protocol than the communication protocol associated with first signal received by IMD 16 response to receiving the first signal. The communication protocol of communication protocols 42 used to transmit the second signal may be the BTLE protocol operating in the normal power mode. In some examples, the second signal includes a set of advertisements which are transmitted by IMD 16 at a second advertisement rate, where the second advertisement rate is significantly higher than the first advertisement rate in which communication circuitry 38 transmits advertisements before IMD 16 receives the first signal. In other examples, communication circuitry 38 does not transmit advertisements before IMD 16 receives the first signal, and communication circuitry 38 transmits the second signal including set of advertisements at the second advertisement rate after IMD 16 receives the first signal.

In response to transmitting the second signal, IMD 16 may receive, in some examples, a first set of random data from external device 18. In other examples, IMD 16 receives the first set of random data from external device 20 over communication link 26. Subsequently, IMD 16 may generate a second set of random data. IMD 16 is configured to transmit the second set of random data, a non-encrypted challenge, and a first encryption key to any combination of external devices 18, 20 according to the reduced power mode of the second protocol. In some examples, IMD 16 transmits the second set of random data, the non-encrypted challenge, and the first encryption key, where the transmission has a signal strength of less than about 150 nW. Transmitting the second set of random data, the non-encrypted challenge, and the first encryption key at less than about 150 nW may limit the range of the transmission to about 1 meter, thus decreasing a probability that the second set of random data, the non-encrypted challenge, or the first encryption key could be intercepted by an untrusted device other than external device 18 and external device 20. In some examples, the first encryption key includes the encrypted form of the device key that is stored in memory 40 as part of encryption keys 46. Using the first set of random data, the second set of random data, and the non-encrypted form of the device key, IMD 16 may generate a second encryption key. The second encryption key may be a 128-bit "session" key that enables IMD 16 to encrypt and decrypt data exchanged with external device 18 and/or external device 20. IMD 16 may store the second encryption key in memory 40 as part of encryption keys 46.

IMD 16 may receive an encrypted challenge from either external device 18 or external device 20, and IMD 16 may decrypt the encrypted challenge using the second encryption key. To verify the challenge, IMD 16 may cross-reference the challenge received from either external device 18 or external device 20 with the non-encrypted challenge originally sent to external device 18. After verifying the challenge, IMD 16 is configured to transmit a verification signal and establish a secure link with external device 18 and/or external device 20.

The second encryption key may be set to expire after a period of time. In some examples, IMD 16 starts a time window after establishing a secure link, where the time window is set to expire after a predetermined amount of time. When the time window expires, IMD 16 terminates the secure link. After a secure link is established between IMD 16 and another device such as external device 18 and/or external device 20, IMD 16 may send and receive data over the secure link. IMD 16 may, for example, receive encrypted data indicative of instructions from external device 20. As such, processing circuitry 30 may use encryption keys 46 (e.g., the second encryption key) to decode the encrypted data and implement the instructions in IMD 16. For example, the instructions may include a request for IMD 16 to output at least some of collected data 45. Additionally, or alternatively, the instructions may cause processing circuitry 30 to record patient data using a particular combination of electrodes 34 and sensors 35. The instructions may also include a request for IMD 16 to output other information, such as a battery life of power source 48, or impedance values of electrodes 34.

Secure communications between IMD 16 and other devices may occur according to at least one of communication protocols 42. As such, other devices communicating with IMD 16 may concurrently be configured with least one of communication protocols 42.

Power source 48 is configured to deliver operating power to the components of IMD 16. Power source 48 may include a battery and a power generation circuit to produce the operating power. In some examples, the battery is rechargeable to allow extended operation. In some examples, recharging is accomplished through proximal inductive interaction between an external charger and an inductive charging coil within external device 18. Power source 48 may include any one or more of a plurality of different battery types, such as nickel cadmium batteries and lithium ion batteries.

Figure 3:
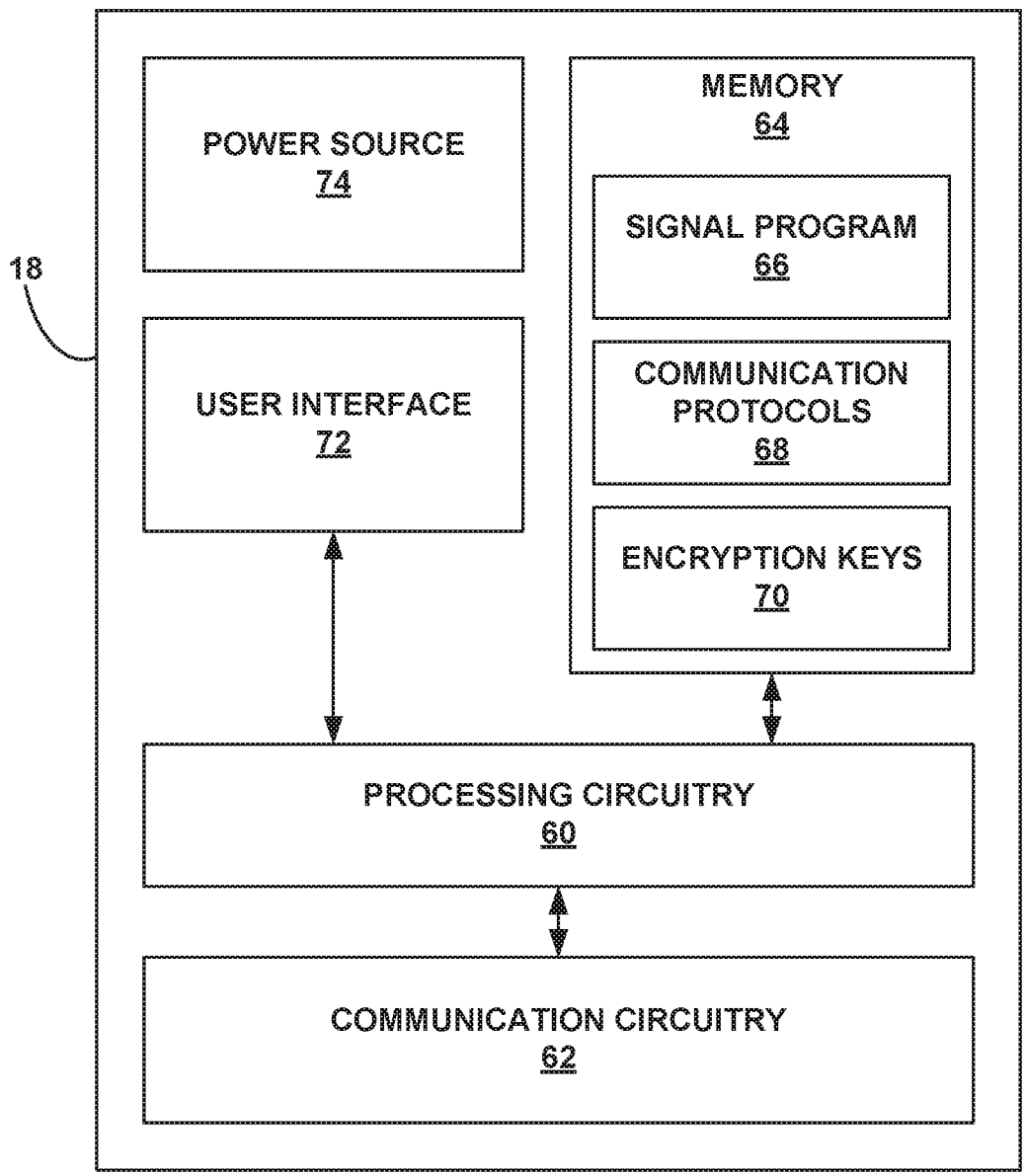
FIG. 3 is a block diagram illustrating an example configuration of components of an example external device, in accordance with one or more techniques of this disclosure.

FIG. 3 is a block diagram illustrating an example configuration of components of external device 18 in accordance with one or more techniques of this disclosure. In the example of FIG. 3, external device 18 includes processing circuitry 60, communication circuitry 62, memory 64, user interface 72, and power source 74. Memory 64 is configured to store signal program 66, communication protocols 68, and encryption keys 70.

Processing circuitry 60, in one example, may include one or more processors that are configured to implement functionality and/or process instructions for execution within external device 18. For example, processing circuitry 60 may be capable of processing instructions stored in memory 64. Processing circuitry 60 may include, for example, microprocessors, DSPs, ASICs, FPGAs, or equivalent discrete or integrated logic circuitry, or a combination of any of the foregoing devices or circuitry. Accordingly, processing circuitry 60 may include any suitable structure, whether in hardware, software, firmware, or any combination thereof, to perform the functions ascribed herein to processing circuitry 60.

Communication circuitry 62 may include any suitable hardware, firmware, software or any combination thereof for communicating with another device, such as IMD 16 or external device 20. Under the control of processing circuitry 60, communication circuitry 62 may receive downlink telemetry from, as well as send uplink telemetry to, IMD 16, external device 20, or another device. In addition, processing circuitry 30 may communicate with a computer network, such as the Medtronic CareLink® Network developed by Medtronic, plc, of Dublin, Ireland. Communication circuitry 62 may include any combination of a Bluetooth® radio, an electronic oscillator, frequency modulation circuitry, frequency demodulation circuitry, amplifier circuitry, and power switches such as a MOSFET, a BJT, an IGBT, a JFET, or another element that uses voltage for its control. Communication circuitry 64 may transmit and receive signals via an antenna, e.g., for radiofrequency communication, and/or electrodes for tissue conductance communication.

Memory 64 may be configured to store information within external device 18 during operation. Memory 64 may include a computer-readable storage medium or computer-readable storage device. In some examples, memory 64 includes one or more of a short-term memory or a long-term memory. Memory 64 may include, for example, RAM, DRAM, SRAM, magnetic discs, optical discs, flash memories, or forms of EPROM or EEPROM. In some examples, memory 64 is used to store data indicative of instructions for execution by processing circuitry 60. Memory 64 may be used by software or applications running on external device 18 to temporarily store information during program execution.

In some examples, external device 18 is used to establish a secure connection with IMD 16. For instance, example techniques of this disclosure enable IMD 16 to transmit, via communication circuitry 62, a signal to IMD 16. The signal may represent a wake-up signal for initiating the establishment of a secure link. Processing circuitry 60 is configured to generate the signal based on signal program 66. In some examples, external device 18 transmits the signal in response to receiving an instruction from external device 20. In other examples, external device 18 transmits the signal based on user input to user interface 72.

Memory 64 is configured to store signal program 66. Signal program 66 may include a list of computer readable instructions which cause processing circuitry 60 to generate the signal, where the signal includes a plurality of primary portions defining a first frequency value and a first duration and a plurality of secondary portions defining a second frequency value and a second duration. Processing circuitry 60 is configured to interleave the plurality of primary portions and the plurality of secondary portions such that one primary portion occurs between two consecutive secondary portions and one secondary portion occurs between two consecutive primary portions. However, the first and last frequency portions, whether they are primary portions or secondary portions, are bounded by one frequency portion. In some examples, the first frequency value is about 200 kilohertz (kHz), the second frequency value is about 150 kHz, and the first duration and the second duration are each about 80 microseconds (μs). However, these values are not meant to be limiting. The first frequency value, the second frequency value, the first duration, and the second duration may include any value or range of values. As such, external device 18 is configured to generate the first signal which is defined by an electromagnetic waveform which alternates between two frequency values.

Processing circuitry 60 may transmit, via communication circuitry 62, the signal generated by external device 18 based on signal program 66 to IMD 16. Processing circuitry 60 may transmit the signal according to at least one of communication protocols 68 stored by memory 64. In some examples, at least some of communication protocols 68 are not included in communication protocols 42 of FIG. 1. Put another way, external device 18 may have access to at least one communication protocol that is not available to IMD 16. In some examples, processing circuitry 60 transmits the signal generated based on signal program 66 to IMD 16 according to a communication protocol that is not available to IMD 16. In some examples, the protocol includes any communication protocol which uses magnetic induction communication, RF communication, or tissue conductance communication.

After transmitting the signal, external device 18 may receive a subsequent signal from IMD 16 which includes a set of advertisements, where the subsequent signal is received by external device 18 according to at least one of communication protocols 68. In some examples, the subsequent signal is received according to the BTLE protocol and a power of the subsequent signal may be less than about 150 nW. In some examples, external device 18 relays the set of advertisements to external device 20. Any combination of processing circuitry 60 of external device 18 and processing circuitry 80 of external device 20 is configured to generate a first set of random data and transmit the first set of random data to IMD 16 according to a communication protocol of communication protocols 68, where the communication protocol is concurrently stored in memory 40 of IMD 16. In examples where external device 20 generates the first set of random data, external device 18 may relay the first set of random data from external device 20 to IMD 16.

After the first set of random data is transmitted to IMD 16, external device 18 may receive a second set of random data, a non-encrypted challenge, and an encrypted form of a first encryption key from IMD 16. In some examples, external device 18 in turn transmits the second set of random data, a non-encrypted challenge, and an encrypted form of a first encryption key to external device 20. As such, any combination of external devices 18, 20 may decrypt the first encryption key to obtain a non-encrypted form of the first encryption key. In some examples, external devices 18, 20 calculate a second encryption key based on the first set of random data, the second set of random data, and the non-encrypted form of the first encryption key. Additionally, external devices 18, 20 may encrypt the challenge and transmit the encrypted challenge to IMD 16. If IMD 16 is able to verify the challenge, external device 18 may receive a verification signal from IMD 16 and establish a secure link with IMD 16. After establishing the secure link, external device 18 is configured to, in one example, relay data between external device 20 and IMD 16 using secure connections.

A user, such as a clinician or patient 4, may interact with external device 18 through user interface 72. User interface 72 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 60 of external device 18 and provide input. In one example, user interface 72 includes a single button which enables the user to instruct external device 18 to execute one or more actions. In other examples, user interface 72 also includes audio circuitry for accepting audio instructions.

Power source 74 is configured to deliver operating power to the components of external device 18. Power source 74 may include a battery and a power generation circuit to produce the operating power. In some examples, the battery is rechargeable to allow extended operation. Recharging may be accomplished by electrically coupling power source 74 to a cradle or plug that is connected to an alternating current (AC) outlet. In addition, recharging may be accomplished through proximal inductive interaction between an external charger and an inductive charging coil within external device 18. In other examples, traditional batteries (e.g., nickel cadmium or lithium ion batteries) may be used. In addition, external device 18 may be directly coupled to an alternating current outlet to operate.

Figure 4:
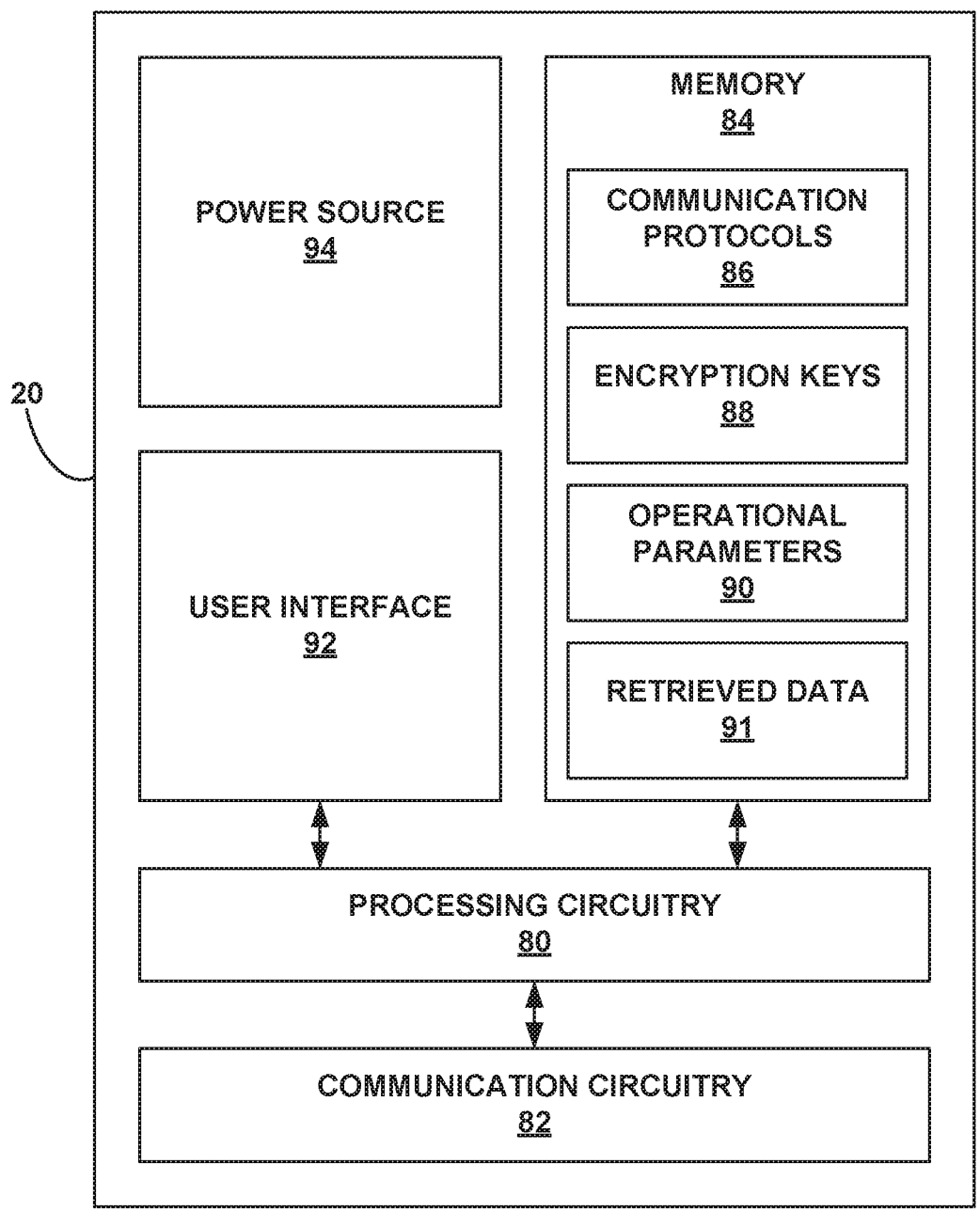
FIG. 4 is a block diagram illustrating an example configuration of components of another example external device, in accordance with one or more techniques of this disclosure.

FIG. 4 is a block diagram illustrating an example configuration of components of external device 20 in accordance with one or more techniques of this disclosure. In the example of FIG. 4, external device 20 includes processing circuitry 80, communication circuitry 82, memory 84, user interface 92, and power source 94. Memory 84 is configured to store communication protocols 86, encryption keys 88, operational parameters 90, and retrieved data 91.

Processing circuitry 80, in one example, may include one or more processors that are configured to implement functionality and/or process instructions for execution within external device 20. For example, processing circuitry 80 may be capable of processing instructions stored in memory 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 16 or external device 18. Under the control of processing circuitry 80, communication circuitry 82 may receive downlink telemetry from, as well as send uplink telemetry to, IMD 16, external device 18, or another device. In some examples, communication circuitry 82 includes a first set of communication circuitry configured for transmitting and receiving signals according to a communication protocol developed by the manufacturer of IMD 16 or a third-party developer. In some such examples, communication circuitry 82 further includes a second set of communication circuitry which defines a Bluetooth® radio configured for transmitting and receiving signals according to Bluetooth® communication protocols. However, communication circuitry 82 does not necessarily include separate sets of circuitry corresponding to different communication protocols. In some examples, communication circuitry 82 includes a single set of circuitry configured for transmitting and receiving signals according to a plurality of communication protocols.

In some examples, communication circuitry 82 includes any combination of a Bluetooth® radio, an electronic oscillator, frequency modulation circuitry, frequency demodulation circuitry, amplifier circuitry, and power switches such as a MOSFET, a BJT, an IGBT, a JFET, or another element that uses voltage for its control.

Memory 84 may be configured to store information within external device 20 during operation. Memory 84 may include a computer-readable storage medium or computer-readable storage device. In some examples, memory 84 includes one or more of a short-term memory or a long-term memory. Memory 84 may include, for example, RAM, DRAM, SRAM, magnetic discs, optical discs, flash memories, or forms of EPROM or EEPROM. In some examples, memory 84 is used to store data indicative of instructions for execution by processing circuitry 80. Memory 84 may be used by software or applications running on external device 20 to temporarily store information during program execution.

External device 20 may exchange information with other devices via communication circuitry 82 according to one or more communication protocols 86. Communication protocols 86, stored in memory 84, may include sets of computer-readable instructions that determine how data is transmitted and processed. Communication protocols 86 may include one or more communication protocols that are additionally included in each of communication protocols 42 and communication protocols 68. In other words, IMD 16, external device 18, and external device 20 may be configured to exchange information according to at least one common communication protocol. In some examples, the one or more common communication protocols include at least one Bluetooth® communication protocol. Additionally, or alternatively, communication protocols 86 may include a set of communication protocols that are not available to at least one of IMD 16 and external device 18. In some examples, external device 20 is a consumer electronics device, such as a smartphone, a tablet, or a laptop computer. In some such examples, external device 20 may not be configured with communication protocols developed by the manufacturer of IMD 16.

External device 20 may transmit data using a secure link. For example, external device 20 may use at least one of encryption keys 88 stored in memory 84 to encode data for transmission to another device via communication circuitry 82 or decode data received from another device via communication circuitry 82. To securely transmit data to another device (e.g., IMD 16), external device 20 may encode the data using an encryption key, where IMD 16 is configured to decode the data using another encryption key which is a counterpart of the encryption key used by external device 20. In cases where external device 20 does not have access to an encryption key which has a counterpart stored in IMD 16, external device 18 is configured to establish a secure link between IMD 16 and external device 20, where external device 18 acts as an intermediary between IMD 16 and external device 20.

In some examples, external device 20 calculates, using processing circuitry 80, a "session" key, where the session key is associated with a counterpart session key stored in IMD 16. For example, external device 20 may calculate the session key using a first set of random data, a second set of random data, and a device key. Processing circuitry 80 may, in some cases, generate the first set of random data or receive the first set of random data from external device 18 via communication circuitry 82. Additionally, processing circuitry 80 may receive the second set of random data and the device key from IMD 16 via external device 18. Processing circuitry 80 may store the session key in memory 84. After creating the session key, processing circuitry 80 is configured to encode data for transmission to IMD 16 using the session key. By the same token, processing circuitry 80 is configured to decode data received from IMD 16, the data encrypted using the counterpart session key stored by IMD 16. In other examples, external device 20 is configured to encode data for transmission to external device 18 using an encryption key of encryption keys 88, where the encryption key possesses a counterpart key stored in memory 64 of external device 18 as a part of encryption keys 70. Subsequently, external device 18 may decode the data, encode the data again using a session key, and transmit the data to IMD 16 which possesses a counterpart session key. In examples where external device 20 creates the session key and in examples where external device 20 does not create the session key, external device 18 is configured to securely relay data between IMD 16 and external device 20.

Data exchanged between external device 20 and IMD 16 may include any of operational parameters 90 stored in memory 84. External device 20 may transmit data including computer readable instructions which, when implemented by IMD 16, may control IMD 16 to change one or more operational parameters according to operational parameters 90 and/or export collected data. For example, processing circuitry 80 may transmit an instruction to IMD 16 which requests IMD 16 to export collected data (e.g., a portion of collected data 45) to external device 20. In turn, external device 20 may receive the collected data from IMD 16 and store the collected data in memory 84 (e.g., as retrieved data 91). Additionally, or alternatively, processing circuitry 80 may export instructions to IMD 16 requesting IMD 16 to update electrode combinations for stimulation or sensing according to operational parameters 90.

A user, such as a clinician or patient 4, may interact with external device 20 through user interface 92. User interface 92 includes a display (not shown), such as an LCD or LED display or other type of screen, with which processing circuitry 80 may present information related to IMD 16 (e.g., EGM signals obtained from at least one electrode or at least one electrode combination). In addition, user interface 92 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 20 and provide input. In other examples, user interface 92 also includes audio circuitry for providing audible notifications, instructions or other sounds to patient 4, receiving voice commands from patient 4, or both. Memory 84 may include instructions for operating user interface 92 and for managing power source 94.

Power source 94 is configured to deliver operating power to the components of external device 20. Power source 94 may include a battery and a power generation circuit to produce the operating power. In some examples, the battery is rechargeable to allow extended operation. Recharging may be accomplished by electrically coupling power source 94 to a cradle or plug that is connected to an alternating current (AC) outlet. In addition, recharging may be accomplished through proximal inductive interaction between an external charger and an inductive charging coil within external device 20. In other examples, traditional batteries (e.g., nickel cadmium or lithium ion batteries) may be used. In addition, external device 20 may be directly coupled to an alternating current outlet to operate.

Figure 5:
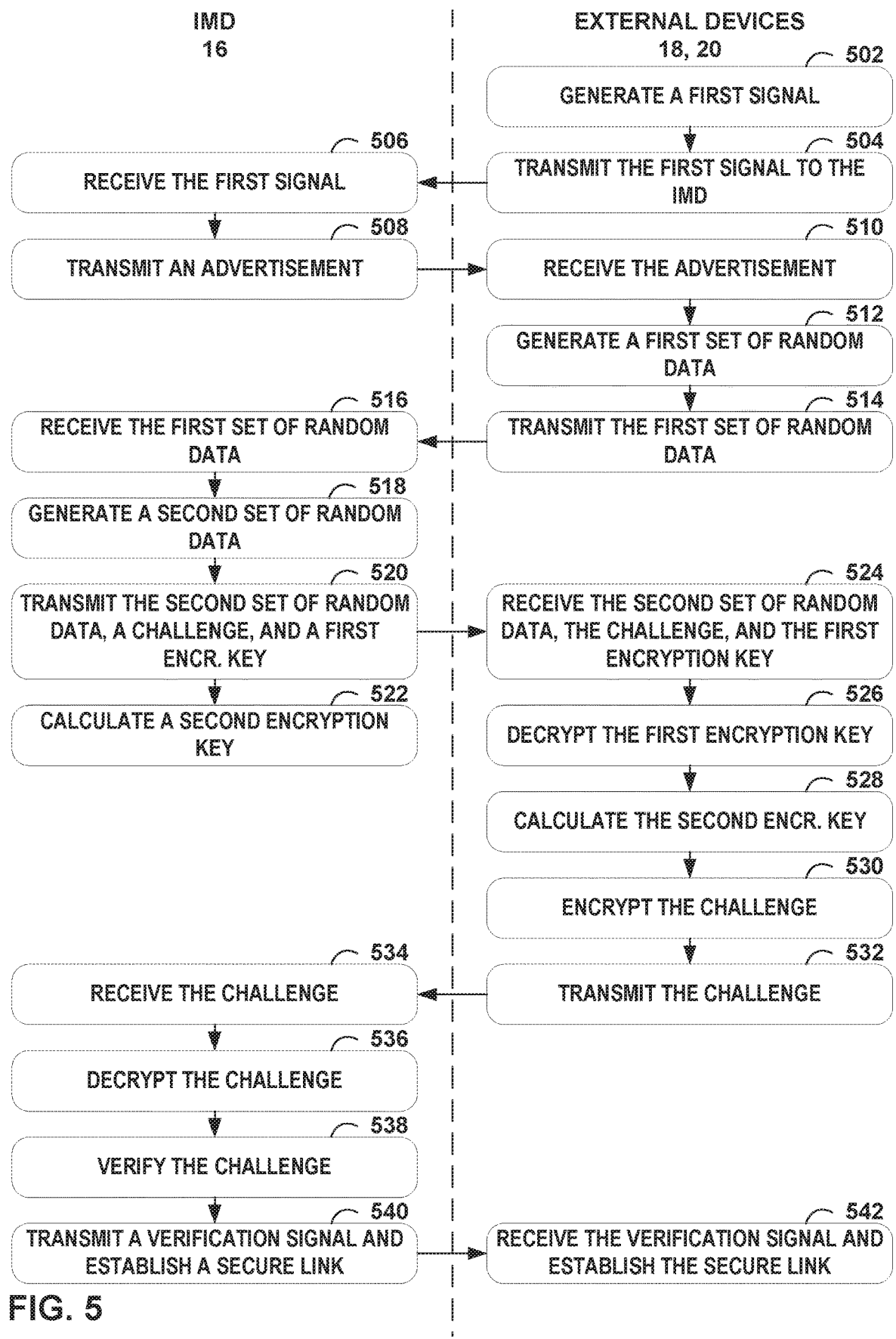
FIG. 5 is a flow diagram illustrating an example operation in accordance with one or more techniques of this disclosure.

FIG. 5 is a flow diagram illustrating an example operation in accordance with one or more techniques of this disclosure. The example operation is described with respect to IMD 16, external device 18, and external device 20 of FIGS. 1-4, and components thereof.

External device 18 is configured to generate a first signal (502). For example, processing circuitry 60 of external device 18 may generate the first signal, where processing circuitry 60 is electrically coupled to communication circuitry 62 configured for wireless communication according to a first protocol and a second protocol. In some examples, external device 18 is configured to generate the first signal based on a signal program 66 stored in memory 64 of external device 18. In some examples the first signal generated by processing circuitry 60 includes a plurality of primary portions defining a first frequency value and a first duration and a plurality of secondary portions defining a second frequency value and a second duration. Processing circuitry 60 is configured to interleave the plurality of primary portions and the plurality of secondary portions such that one primary portion occurs between two consecutive secondary portions and one secondary portion occurs between two consecutive primary portions. However, the first and last frequency portions of the first signal, whether they are primary portions or secondary portions, are bounded by one frequency portion. In some examples, the first frequency value is about 200 kilohertz (kHz), the second frequency value is about 150 kHz, and the first duration and the second duration are each about 80 microseconds (μs). However, these values are not meant to be limiting. The first frequency value, the second frequency value, the first duration, and the second duration may include any value or range of values. As such, external device 18 is configured to generate the first signal which is defined by an electromagnetic waveform which alternates between two frequency values.

After generating the first signal, external device 18 is configured to transmit the first signal to IMD 16 (504). In some examples, external device 18 transmits the first signal according to the first protocol, which is included in communication protocols 68 stored in memory 64. In some examples, the first protocol includes any communication protocol which uses magnetic induction communication, RF communication, or tissue conductance communication. IMD 16 receives the first signal (506). Even though, in some examples, IMD 16 is not configured for the first protocol associated with the first signal, IMD 16 may be configured to detect the first signal by detecting electromagnetic field variations. Signal reception circuitry 37 of IMD 16 may include circuitry capable of sensing such electromagnetic field variations caused by the first signal. Additionally, processing circuitry 30 of IMD 16 is configured to identify one or more parameters of the first signal based on the electromagnetic field variations sensed by signal reception circuitry 37. By comparing the one or more parameters of the first signal with one or more known parameters stored in memory 40 of IMD 16, processing circuitry is 30 configured to verify that the first signal was transmitted by a trusted device (e.g., external device 18).

In response to receiving the first signal and verifying that the first signal originated from external device 18, IMD 16 is configured to transmit a set of advertisements (508) via a second signal. In some examples, IMD 16 is configured to transmit the second signal including the set of advertisements according to the second protocol which is stored as part of communication protocols 42 in memory 40. The second protocol may include a Bluetooth® protocol such as a BTLE protocol having a reduced power mode and a normal power mode. In some examples, IMD 16 is configured to transmit the second signal according to the second protocol when IMD 16 is operating in the normal power mode. In other examples, IMD 16 is configured to transmit the second signal according to the second protocol when IMD 16 is operating in the reduced power mode. In some examples, prior to transmitting the set of advertisements via the second signal, IMD 16 transmits advertisements at a first advertisement rate. Additionally, IMD 16 may transmit the set of advertisements via the second signal at a second advertisement rate, where the second advertisement rate is greater than the first advertisement rate. In this way, receiving the first signal may cause IMD 16 to increase a rate in which IMD 16 transmits advertisements. However, in other examples, IMD 16 does not transmit any advertisements before receiving the first signal and IMD 16 initiates the transmission of advertisements after receiving the first signal.

External devices 18, 20 are configured to receive at least one of the set of advertisements (510), in some cases according to the second protocol stored in memory 64. In response to receiving the set of advertisements, any combination of external devices 18, 20 are configured to generate a first set of random data (512) and transmit the first set of random data (514) to IMD 16 according to, in some examples, the second protocol. In examples where external device 20 generates the first set of random data, external device 18 may relay the first set of random data from external device 20 to IMD 16. In some examples, external device 18 transmits the first set of random data to IMD 16 according to the second protocol while external device 18 is operating in the reduced power mode. In other examples, external device 18 transmits the first set of random data to IMD 16 according to the second protocol while external device 18 is operating in the normal power mode.

After IMD 16 receives the first set of random data (516), IMD 16 generates a second set of random data (518). In one example, the first set of random data and the second set of random data are both 64-bit integers. Subsequently, IMD 16 is configured to transmit the second set of random data, a challenge, and a first encryption key (520) to external devices 18, 20 according to the second protocol. In some examples, IMD 16 is configured to transmit the second set of random data, the challenge, and the first encryption key to external devices 18, 20 according to the second protocol when IMD 16 is operating in the reduced power mode. For example, while operating in the reduced power mode, IMD 16 may transmit the second set of random data, the challenge, and the first encryption key such that the transmission has a maximum signal strength of 150 nW, thus limiting the range of the transmission to 1 meter. In some examples, the challenge is a 64-bit random integer and the first encryption key is a 113-byte "device" key. In some examples, an encrypted version of the first encryption key and a non-encrypted version of the first encryption key are both stored as part of encryption keys 46 in memory 40 of IMD 16. The encrypted form of the first encryption key may, in some examples, be encrypted using the Elliptic Curve Integrated Encryption Scheme (ECIES). In some examples, to prevent the first encryption key from being intercepted or otherwise compromised, IMD 16 transmits the encrypted version of the first encryption key to external devices 18, 20.

Based on the first set of random data, the second set of random data, and the non-encrypted version of the first encryption key, IMD 16 is configured to calculate a second encryption key (522). The second encryption key may, in some examples, define a "session" key.

External devices 18, 20 receive the second set of random data, the challenge, and the encrypted version of the first encryption key (524) from IMD 16. In some examples, external device 18 receives the second set of random data, the challenge, and the encrypted version of the first encryption key and relays the second set of random data, the challenge, and the encrypted version of the first encryption key to external device 20. In other examples, external device 18 receives the second set of random data, the challenge, and the encrypted version of the first encryption key and does not transmit the second set of random data, the challenge, and the encrypted version of the first encryption key to external device 20. In other examples, external device 20 directly receives the second set of random data, the challenge, and the encrypted version of the first encryption key from IMD 16, thus bypassing external device 18.

Any combination of external devices 18, 20 decrypt the first encryption key (526) to obtain the non-encrypted version of the first encryption key using, in some examples, an ECIES private key. After external devices 18, 20 decrypt the first encryption key, any combination of external devices 18, 20 calculate the second encryption key (528) based on the first set of random data, the second set of random data, and the non-encrypted version of the first encryption key. As such, each of IMD 16, external device 18, and external device 20 are configured to independently calculate the second encryption key based on the same pieces of data. Such methods of independently calculating the second encryption key may be beneficial since the second encryption key does not need to be exchanged between any of IMD 16, external device 18, and external device 20, thus decreasing a possibility that the second encryption key will become compromised.

As discussed above, IMD 16 is configured to transmit a 64-bit challenge external devices 18, 20. The challenge is, in some cases, not encrypted when it is transmitted from IMD 16 to external devices 18, 20. External device 18, external device 20, or any combination thereof are configured to encrypt the challenge (530) using the second encryption key and transmit the challenge (532) back to IMD 16 in encrypted form. External devices 18, 20 may transmit the challenge to IMD 16 according to the second protocol. In some examples, external device 18 transmits the challenge to IMD 16 according to the second protocol while external device 18 is operating in the normal power mode. In other examples, external device 18 transmits the challenge to IMD 16 according to the second protocol while external device 18 is operating in the reduced power mode. IMD 16 receives the challenge (534) and decrypts the challenge (536) using the second encryption key. After decrypting the challenge, IMD 16 verifies the challenge (538) by cross-referencing the decrypted challenge with the challenge originally transmitted to external devices 18, 20. IMD 16 proceeds to transmit a verification signal and establish a secure link with external devices 18, 20 (540). In some examples, IMD 16 transmits the verification according to the second protocol while IMD 16 is operating in the normal power mode. In other examples, IMD 16 transmits the verification according to the second protocol while IMD 16 is operating in the reduced power mode. External devices 18, 20 receive the verification signal and establish the secure link with IMD 16 (542). In some examples, external device 18 generates the session key and relays data between IMD 16 and external device 20, thus acting as an intermediary device. In other examples, external device 20 generates the "session" key (e.g., the second encryption key), enabling external device 20 to enter the secure link established by external device 18 and indirectly exchange data with IMD 16. In some examples, external device 20 transmits a session key to external device 18, allowing external device 18 to communicate independently with IMD 16.

In some examples, while communicating over the secure link, any combination of IMD 16, external device 18, and external device 20 exchange data according to the second protocol, where IMD 16, external device 18, and external device 20 are operating in the normal power mode of the second protocol. In some examples, a power magnitude of signals transmitted by a device operating in the normal power mode is one hundred times greater than signals transmitted by the device operating in the reduced power mode.

Any one or more of IMD 16, external device 18, and external device 20 are configured to, at any time, issue an instruction to terminate the secure link. For example, IMD 16 may issue an instruction to invalidate encryption keys corresponding to the secure link. Additionally, IMD 16, external device 18, or external device 20 may set a time window associated with encryption keys corresponding to the secure link. If the time window reaches a predetermined expiration time, the secure link may be terminated.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A device configured for wireless communication, wherein the device comprises:
   signal reception circuitry configured to receive communications transmitted according to at least a first communication protocol;
   communication circuitry configured to send communications and receive communications according to at least a second communication protocol different than the first communication protocol; and
   processing circuitry electrically coupled to the signal reception circuitry and the communication circuitry, wherein the processing circuitry is configured to:
      receive, from one or more external devices via the signal reception circuitry, a first signal according to the first communication protocol;
      in response to receiving the first signal, transmit, via the communication circuitry, a second signal including a set of advertisements according to the second communication protocol;
      in response to transmitting the second signal including the set of advertisements, receive, from the one or more external devices, a first set of random data according to the second communication protocol;
      generate a second set of random data;
      transmit the second set of random data, a challenge, and a first encryption key to the one or more external devices according to the second communication protocol at a first power magnitude, wherein the first power magnitude is less than a second power magnitude, wherein the first encryption key is encrypted, and wherein the challenge is not encrypted;
      calculate, based on the first set of random data, the second set of random data, and the first encryption key, a second encryption key;
      receive, from the one or more external devices, the challenge according to the second communication protocol, wherein the challenge is encrypted;

decrypt the challenge using the second encryption key;
verify the challenge by comparing the decrypted challenge with the transmitted challenge; and
transmit, to the one or more external devices according to the second communication protocol, a verification signal which confirms that the challenge is verified and establishes a secure link between the device and the one or more external devices according to the second communication protocol, and
wherein communications transmitted over the established secure link are according to the second communication protocol at the second power magnitude.

2. The device of claim 1, wherein the device is not configured to send communications according to the first communication protocol.

3. The device of claim 1, wherein the first power magnitude is less than about 150 nanowatts (nW).

4. The device of claim 1, wherein the first communication protocol includes a magnetic induction communication protocol, a radio frequency (RF) communication protocol, or a tissue conductance communication (TCC) protocol.

5. The device of claim 1, wherein the second communication protocol comprises a Bluetooth® Low Energy (BTLE) protocol having a reduced power mode and a normal power mode, wherein signals transmitted according to the second communication protocol operating in the reduced power mode are transmitted at the first power magnitude, and wherein signals transmitted according to the second communication protocol operating in the normal mode are transmitted at the second power magnitude.

6. The device of claim 1, wherein the second encryption key comprises an advanced encryption standard (AES) key, and wherein the second encryption key defines a size of 128 bits.

7. The device of claim 1, wherein in response to receiving the first signal, the device is configured to transmit the second signal including the set of advertisements for a period of time lasting up to a time limit of 30 seconds.

8. The device of claim 1, wherein the device is a first device, wherein the first signal is from a second device, wherein the second signal is sent to the second device, and wherein the secure link comprises a secure link between the device and at least one of the second device or a third device, and wherein the one or more external devices comprise the second device and the third device.

9. The device of claim 1, wherein the first signal comprises a wake-up signal for the device according to the first communication protocol, and wherein based on receiving the first signal, the processing circuitry is configured to transition the communication circuitry from a relatively lower energy consumption mode to a relatively higher energy consumption mode.

10. The device of claim 9, wherein to transition the communication circuitry from the relatively lower energy consumption mode to the relatively higher energy consumption mode, the processing circuitry configured to increase a rate in which the device transmits advertisements from a first advertisement rate to a second advertisement rate.

11. The device of claim 10, wherein the first advertisement rate is greater than twenty advertisements per hour and less than sixty advertisements per hour, and wherein the second advertisement rate is greater than one advertisement per second.

12. The device of claim 10, wherein the first advertisement rate is zero advertisements per second, and wherein the second advertisement rate is greater than one advertisement per second.

13. The device of claim 1, wherein the first signal comprises:
a plurality of primary portions, wherein each primary portion of the plurality of primary portions defines a first frequency value and a first duration; and
a plurality of secondary portions, wherein each secondary portion of the plurality of secondary portions defines a second frequency value and a second duration, wherein the plurality of primary portions and the plurality of secondary portions are interleaved such that one primary portion occurs between two consecutive secondary portions and one secondary portion occurs between two consecutive primary portions, and
wherein the processing circuitry is further configured to:
in response to receiving the first signal, authenticate the first signal by matching at least one of the first frequency value, the second frequency value, the first duration, and the second duration to known values stored by the device.

14. The device of claim 1, wherein the first signal transmitted according to the first communication protocol includes a transmission range of less than about 20 centimeters (cm).

15. The device of claim 1, wherein the first power magnitude is within a range from −50 decibels with reference to one milliwatt (dBm) to −10 dBm, and wherein the second power magnitude is 0 dBm.

16. The device of claim 1, wherein the device comprises an implantable medical device (IMD).

17. A method comprising:
receiving, by signal reception circuitry of a device configured to receive communications transmitted according to at least a first communication protocol, a first signal from one or more external devices according to the first communication protocol;
in response to receiving the first signal, transmitting, via communication circuitry configured to send communications and receive communications according to at least a second communication protocol different from the first communication protocol, a second signal including a set of advertisements according to the second communication protocol;
in response to transmitting the second signal including the set of advertisements, receiving, by processing circuitry electrically coupled to the signal reception circuitry and the communication circuitry, a first set of random data from the one or more external devices according to the second communication protocol;
generating, by the processing circuitry, a second set of random data;
transmitting, by the processing circuitry, the second set of random data, a challenge, and a first encryption key to the one or more external devices according to the second communication protocol at a first power magnitude, wherein the first power magnitude is less than a second power magnitude, wherein the first encryption key is encrypted, and wherein the challenge is not encrypted;
calculating, by the processing circuitry based on the first set of random data, the second set of random data, and the first encryption key, a second encryption key;
receiving, by the processing circuitry from the one or more external devices, the challenge according to the second communication protocol, wherein the challenge is encrypted;
decrypting, by the processing circuitry, the challenge using the second encryption key;

verifying, by the processing circuitry, the challenge by comparing the decrypted challenge with the transmitted challenge; and transmitting, by the processing circuitry to the one or more external devices according to the second communication protocol, a verification signal which confirms that the challenge is verified and establishes a secure link between the device and the one or more external devices according to the second communication protocol, wherein communications transmitted over the established secure link are according to the second communication protocol at the second power magnitude.

18. The method of claim 17, wherein the device is not configured to send communications according to the first communication protocol.

19. The method of claim 17, wherein the first power magnitude is less than about 150 nanowatts (nW).

20. The method of claim 17, wherein calculating the second encryption key comprises calculating an advanced encryption standard (AES) key, and wherein the AES key defines a size of 128 bits.

21. The method of claim 17, wherein in response to receiving the first signal, the method further comprises transmitting the second signal including the set of advertisements for a period of time lasting up to a time limit of 30 seconds.

22. The method of claim 17, wherein the device is a first device, wherein the first signal is from a second device, wherein the second signal is sent to the second device, and wherein establishing the secure link comprises establishing the secure link which includes the first device and at least one of the second device or a third device.

23. The method of claim 17, wherein the first signal comprises:
a plurality of primary portions, wherein each primary portion of the plurality of primary portions defines a first frequency value and a first duration; and
a plurality of secondary portions, wherein each secondary portion of the plurality of secondary portions defines a second frequency value and a second duration, wherein the plurality of primary portions and the plurality of secondary portions are interleaved such that one primary portion occurs between two consecutive secondary portions and one secondary portion occurs between two consecutive primary portions, and
wherein the method further comprises:
in response to receiving the first signal, authenticating the first signal by matching at least one of the first frequency value, the second frequency value, the first duration, and the second duration to known values stored by the device.

24. The method of claim 17, wherein the first signal transmitted according to the first communication protocol includes a transmission range of less than about 20 centimeters (cm).

25. The method of claim 17, wherein the device comprises an implantable medical device (IMD).

26. A system comprising:
a first device comprising:
signal reception circuitry configured to receive communications transmitted according to at least a first communication protocol;
first communication circuitry configured to send communications and receive communications according to at least a second communication protocol different from the first communication protocol; and
first processing circuitry electrically coupled to the signal reception circuitry and the first communication circuitry, wherein the first processing circuitry is configured to:
receive, from one or more external devices via the signal reception circuitry, a first signal according to the first communication protocol; and
in response to receiving the first signal, transmit, via the first communication circuitry, a second signal including a set of advertisements according to the second communication protocol;
in response to transmitting the second signal including the set of advertisements, receive, from the one or more external devices, a first set of random data according to the second communication protocol;
generate a second set of random data;
transmit the second set of random data, a challenge, and a first encryption key to the one or more external devices according to the second communication protocol at a first power magnitude, wherein the first power magnitude is less than a second power magnitude, wherein the first encryption key is encrypted, and wherein the challenge is not encrypted;
calculate, based on the first set of random data, the second set of random data, and the first encryption key, a second encryption key;
receive, from the one or more external devices, the challenge according to the second communication protocol, wherein the challenge is encrypted;
decrypt the challenge using the second encryption key;
verify the challenge by comparing the decrypted challenge with the transmitted challenge; and
transmit, to the one or more external devices according to the second communication protocol, a verification signal which confirms that the challenge is verified and establishes a secure link between the device and the one or more external devices according to the second communication protocol; and
a second device comprising:
second communication circuitry configured to send communications according to the first communication protocol having a first range and the second communication protocol having a second range, the second communication protocol different than the first communication protocol and the second range greater than the first range; and
second processing circuitry electrically coupled to the second communication circuitry, wherein the one or more external devices comprise the second device, and wherein the second processing circuitry is configured to:
transmit, via the second communication circuitry, the first signal to the first device according to the first communication protocol;
in response to transmitting the first signal, receive, via the second communication circuitry and from the first device, the second signal according to the second communication protocol;
generate a first set of random data;
transmit, to the first device, via the second communication circuitry, the first set of random data according to the second communication protocol;

receive the second set of random data, the challenge, and the first encryption key from the first device according to the second communication protocol at the first power magnitude;
decrypt the first encryption key;
calculate the second encryption key based on the first set of random data, the second set of random data, and the decrypted first encryption key;
encrypt the challenge based on the second encryption key;
transmit the challenge to the first device; and
in response to transmitting the challenge, receive the verification signal which confirms that the challenge is verified and establishes a secure link according to the second communication protocol, and
wherein communications transmitted over the established secure link are according to the second communication protocol at the second power magnitude.

* * * * *